United States Patent
Springer et al.

(10) Patent No.: US 8,642,659 B2
(45) Date of Patent: Feb. 4, 2014

(54) HAIR TREATMENT PRODUCT AND HAIR AFTER-TREATMENT PRODUCT CONTAINING ETHER GUANIDINES AS ACTIVE SUBSTANCES, FOR PROTECTING FROM DAMAGE CAUSED BY CHEMICAL TREATMENT AND FOR REPAIRING ALREADY DAMAGED HAIR

(75) Inventors: Oliver Springer, Wesel (DE); Peter Muss, Essen (DE); Burghard Gruening, Essen (DE); Ursula Maczkiewitz, Essen (DE); Mike Farwick, Essen (DE); Peter Lersch, Dinslaken (DE)

(73) Assignee: Evonik Goldschmidt GmbH, Essen (DE)

( * ) Notice: Subject to any disclaimer, the term of this patent is extended or adjusted under 35 U.S.C. 154(b) by 314 days.

(21) Appl. No.: 13/001,562

(22) PCT Filed: May 28, 2009

(86) PCT No.: PCT/EP2009/056492
§ 371 (c)(1),
(2), (4) Date: Dec. 27, 2010

(87) PCT Pub. No.: WO2009/156241
PCT Pub. Date: Dec. 30, 2009

(65) Prior Publication Data
US 2011/0117219 A1     May 19, 2011

(30) Foreign Application Priority Data
Jun. 27, 2008 (DE) .......................... 10 2008 002 707

(51) Int. Cl.
*A61K 31/155* (2006.01)
*C07C 279/02* (2006.01)

(52) U.S. Cl.
USPC ......................................... 514/634; 564/230

(58) Field of Classification Search
None
See application file for complete search history.

(56) References Cited

U.S. PATENT DOCUMENTS

2005/0136017 A1    6/2005   Malle et al.

FOREIGN PATENT DOCUMENTS

| EP | 1 671 615 A2 | 6/2006 |
| JP | 11-35546 | 2/1999 |
| JP | 11-035546 | * 2/1999 |

OTHER PUBLICATIONS

English Translation of JP 11-035546 (Feb. 1999), machine translated on Nov. 26, 2012.*
International Search Report, mailed Nov. 18, 2009.
Air Products and Chemicals Inc., Tomamine Ether Amines Product Guide, Air Products, Allentown USA, Mar. 2012, XP002553897.

* cited by examiner

*Primary Examiner* — James D Anderson
(74) *Attorney, Agent, or Firm* — Scully, Scott, Murphy & Presser P.C.

(57) ABSTRACT

The invention relates to ether guanidines of the general formulae (I)

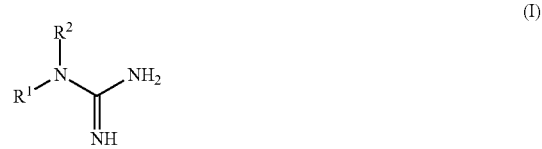

and/or salts or hydrates thereof, in which $R^1 = -CH_2-CH_2-CH_2-O-R^3$ where $R^3$ is, independently of the others, hydrocarbon radicals having greater than or equal to 10 carbon atoms, where part of the ether guanidines has radicals $R^3$ which are branched and part of the ether guanidines has radicals $R^3$ which are unbranched, and $R^2$=independently of the others H or an optionally branched, optionally double-bond-containing hydrocarbon radical having 1 to 30 carbon atoms, and use thereof in hair treatment compositions and hair aftertreatment compositions, in particular for preventing damage by chemical treatment compositions and for repairing hair which is already damaged.

8 Claims, No Drawings

HAIR TREATMENT PRODUCT AND HAIR AFTER-TREATMENT PRODUCT CONTAINING ETHER GUANIDINES AS ACTIVE SUBSTANCES, FOR PROTECTING FROM DAMAGE CAUSED BY CHEMICAL TREATMENT AND FOR REPAIRING ALREADY DAMAGED HAIR

The cosmetic treatment of skin and hair is an important constituent of human body care. Thus, human hair is exposed daily to highly diverse influences. Besides mechanical stresses as a result of brushing, combing, putting up or tying back, the hair is also attacked by environmental influences such as, for example, strong UV radiation, cold, wind and water. The physiological status (e.g. age, health) of the person in question also influences the damage of the keratin fibres.

Thus, human hair is nowadays treated in diverse ways with hair cosmetic preparations. These include, for example, the cleaning of the hair with shampoos, the care and regeneration with rinses and treatments and also bleaching (or synonymously lightening and/or blonding), colouring and shaping the hair using bleaching compositions (or synonymously lightening compositions or blonding compositions), colorants, tinting compositions, waving compositions and styling preparations. Changing the colour of the hair is experiencing increased popularity with consumers. However, the treatment with chemical agents in particular changes the structure and the surface properties of the hair. Thus, for example during a permanent wave, both the cortex and also the cuticle of the hair are attacked. The disulphide bridges of the cystine are broken by the reducing step and oxidized in part to give cysteic acid in the subsequent oxidation step.

During bleaching, not only is the melanin destroyed, but furthermore ca. 15 to 25% by weight of the disulphide bonds of the cystine are oxidized in the event of mild bleaching. In the event of excessive bleaching, it may even be up to 45% by weight (K. F. de Polo, A Short Textbook of Cosmetology, 2000, Verlag für chemische Industrie, H. Ziolkowsky GmbH).

Diverse treatment of the hair, for example by bleaching, colouring, tinting and shaping, but also cleaning of the hair using aggressive shampoos and environmental stresses, can lead to an undesired impairment of the hair structure. The impairment of the hair structure becomes evident, for example, from poor wet and dry combability, increased electrostatic charging, increased brittleness, reduced maximum tear force and elongation at tear of the hair, split ends and an overall poorer outer appearance of the hair. Furthermore, the problem with a large number of cosmetic haircare substances is that they produce excellent results with regard to haircare and hair rinses in test formulations, but lose efficiency in shampoo and/or conditioning formulations because they cannot be incorporated into these formulations in an adequate amount, if at all.

Numerous active ingredients are known which assist haircare and prevent impairments of the hair structure. However, the known active ingredients are not able to meet all of the requirements to an adequate degree.

There is therefore a need for active ingredients and/or active ingredient combinations for cosmetic compositions with good care properties and good biodegradability which can be incorporated into known formulations without problems.

Furthermore, there is a need for haircare compositions which clean and care for the hair without a further hair treatment step with a special haircare composition being necessarily required. On account of the increasing sales numbers of hair colorants which damage the hair structure more and more particularly upon repeated hair colouring or hair bleaching, hair treatment compositions are at the same time desired which reduce hair damage caused by oxidative treatment and restore the hair to a good state with regard to wet and dry combability, shine, softness, volume, feel and hold. At the same time, split ends should be reduced and/or prevented.

In recent times, the use of guanidine compounds and/or derivatives in skin and haircare products has been described. For example, EP 1 493 423 describes the use of alkylguanidine compounds and/or salts thereof in hair treatment compositions and hair aftertreatment compositions for preventing damage by chemical treatment agents and for repairing hair which is already damaged. EP 1 646 429 describes the use of alkylguanidine compounds for the treatment and aftertreatment of hair.

EP 1 671 615 describes emulsions which have cationic emulsifiers based on salt conjugates of guanidine compounds, where these guanidine compounds may also be alkyloxyalkyl guanidine compounds (ether guanidines). These emulsions can also be used for producing haircare compositions.

DE 195 27 313, U.S. Pat. No. 5,723,133 and U.S. Pat. No. 5,939,078 describe ether guanidines which have a maximum of 11 carbon atoms as alkyl radical, and their use as skin cosmetic.

US 2005/0129645 and US 2005/0136017 describe the use of imines in cosmetic compositions, where the imines mentioned are also short-chain ether guanidines, such as, for example, 3-methoxypropylguanidines, or 2-ethoxy-ethylguanidines.

JP 11-035546 describes the use of branched ($C_{12-24}$-alkyloxyl-$C_{1-6}$-alkyl) guanidine derivatives in haircare compositions.

The object of the present was to provide ether guanidines which have improved haircare properties and can be easily incorporated into various formulations.

Surprisingly, it has been found that ether guanidines which have a certain carbon chain length and have both branched and also unbranched alkyl radicals exhibit the desired improved properties.

The present invention therefore provides ether guanidines of the general formula (I)

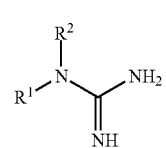

(I)

and/or salts or hydrates thereof, in which
$R^1$=—$CH_2$—$CH_2$—$CH_2$—O—$R^3$ where $R^3$ is, independently of the others, hydrocarbon radicals having greater than or equal to 10 carbon atoms, where part of the ether guanidines has radicals $R^3$ which are branched and part of the ether guanidines has radicals $R^3$ which are unbranched, and
$R^2$=independently of the others H or an optionally branched, optionally double-bond-containing hydrocarbon radical having 1 to 30 carbon atoms.

Likewise provided by the present invention are hair treatment compositions and hair aftertreatment compositions which have the ether guanidines of the invention according to the claims as active substances.

Moreover, the present invention provides the use of the ether guanidines according to the invention or of the hair treatment compositions and hair aftertreatment compositions according to the invention for producing hair rinses, hair shampoos, hair treatments, leave-in conditioners, reviving compositions and setting formulations.

Where the term ether guanidines is used below, this should be understood as meaning not only the ether guanidines themselves, but also salts or hydrates thereof.

The ether guanidines according to the invention have the advantage that they have both good stability and also good formulatability. Moreover, even in low use concentrations, they bring about a marked effect, are nontoxic, are very well tolerated by the hair and the scalp, have high compatibility with other ingredients and can be incorporated into hair treatment compositions and hair aftertreatment compositions without problems. Additionally, they can also have an antimicrobial effect.

The ether guanidines and compositions according to the invention, their preparation and use are described below by way of example without any intention to limit the invention to these exemplary embodiments. Where ranges, general formulae or compound classes are given below, then these are intended to include not only the corresponding ranges or groups of compounds explicitly mentioned, but all other part ranges and part groups of compounds which can be obtained by removing individual values (ranges) or compounds. Where, in the context of the present description, documents are cited, then their content is deemed to belong in its entirety to the disclosure content of the present invention. Where, within the context of the present invention, compounds such as, for example, organomodified polysiloxanes, are described which can have different units several times, then these may be present in these compounds in random distribution (random oligomer or polymer) or arranged (block oligomer or block polymer). Data regarding the number of units in such compounds is to be understood as an average value, averaged over all of the corresponding compounds.

The ether guanidines according to the invention of the general formula (I)

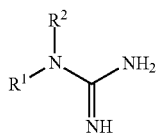

(I)

and/or salts or hydrates thereof, are characterized in that in them
$R^1$=—$CH_2$—$CH_2$—$CH_2$—O—$R^3$ where $R^3$, independently of the others, is hydrocarbon radicals, preferably alkyl radicals, having greater than or equal to 10 carbon atoms, preferably having 11 to 18, preferably 12 to 15, carbon atoms, where part of the ether guanidines has radicals $R^3$ which are branched and part of the ether guanidines has radicals $R^3$ which are unbranched, and
$R^2$=independently of the others H or an optionally branched, optionally double-bond-containing hydrocarbon radical having 1 to 30 carbon atoms, preferably 4 to 22 and preferably 8 to 12 carbon atoms.

Preferred ether guanidines according to the invention are those in which the radicals $R^2$ are exclusively hydrogen atoms.

It may be advantageous if, in the ether guanidines according to the invention, from 50 to 95% by weight, preferably 70 to 90% by weight, preferably 75 to 85% by weight and particularly preferably about 80% by weight, of the ether guanidines have radicals $R^3$ which are unbranched alkyl radicals, and 5 to 50% by weight, preferably 10 to 30% by weight, preferably 15 to 25% by weight and particularly preferably about 20% by weight of the ether guanidines have radicals $R^3$ which are branched alkyl radicals, where the unbranched and branched alkyl radicals preferably have from 12 to 15 carbon atoms.

Preferably, the ether guanidines and/or the mixtures thereof are those in which both alkyl radicals $R^3$ having 12 and also having 13, 14 and 15 carbon atoms are present and these are present in each case in a fraction of from 10 to 50% by weight, preferably 15 to 40% by weight and particularly preferably in a ratio of from 20 to 30% by weight, based on the mass of all alkyl radicals $R^3$.

Particular preference is given to those ether guanidines which are obtained by guanidylation of the ether amine PA-19 from Tomah Products.

As salt, the ether guanidines according to the invention can be, for example, the salt of an organic or inorganic acid. As salt, the ether guanidines according to the invention can be, for example, the salt of at least one of the acids selected from the group of the substituted or unsubstituted, preferably unsubstituted carboxylic acids (mono-, di- and polycarboxylic acids), such as, for example, formic acid, acetic acid, propionic acid, butanoic acid, isobutanoic acid, hexanoic acid, heptanoic acid, octanoic acid, caprylic acid, nonanoic acid, decanoic acid, capric acid, undecanoic acid, lauric acid, myristic acid, palmitic acid, stearic acid, arachic acid, behenic acid, cyclopentanecarboxylic acid, cyclohexane-carboxylic acid, acrylic acid, methacrylic acid, vinylacetic acid, isocrotonic acid, crotonic acid, 2-/3-/4-pentenoic acid, 2-/3-/4-/5-hexenoic acid, lauroleic acid, myristoleic acid, palmitoleic acid, oleic acid, gadoleic acid, sorbic acid, linoleic acid, linolenic acid, pivalic acid, ethoxyacetic acid, phenylacetic acid, glycolic acid, lactic acid, cinnamic acid, sorbic acid, nicotinic acid, urocanic acid, pyrrolidonecarboxylic acid, 2-ethylhexanoic acid, oxalic acid, glycolic acid, malic acid, malonic acid, succinic acid, tartaric acid, glutaric acid, citric acid, adipic acid, pimelic acid, suberic acid, azelaic acid, sebacic acid, maleic acid, fumaric acid, benzoic acid, o-/m-/p-toluic acid, o-/m-/p-hydroxybenzoic acid, salicylic acid, 3-/4-hydroxybenzoic acid, phthalic acid, terephthalic acid, or completely or partially hydrogenated derivatives thereof, such as hexahydro- or tetrahydrophthalic acid, amino acids, such as, for example, glycine, alanine, beta-alanine, valine, leucine, phenylalanine, tyrosine, serine, threonine, methionine, cysteine, cystine, proline, hydroxyproline, pipecolic acid, tryptophan, aspartic acid, asparagine, glutamic acid, glutamine, lysine, histidine, ornithine, arginine, or aminobenzoic acid, alkylsulphonic acids, such as, for example, methanesulphonic acid or trifluoro-methanesulphonic acid, arylsulphonic acids, such as, for example, benzenesulphonic acid or p-toluenesulphonic acid or inorganic acids such as, for example, carbonic acid, phosphoric acid, hydrochloric acid, hydrobromic acid, hydroiodic acid, hydrofluoric acid, perchloric acid, nitric acid or sulphuric acid, and mixtures thereof, preferably the salt of lactic acid, tartaric acid, acetic acid, sulphuric acid or hydrochloric acid and preferably the salt of hydrochloric acid.

The preparation of the ether guanidines can take place in a manner known per se. In particular, the preparation of the ether guanidines can take place in accordance with the preparation of alkylguanidines by guanidylation of the corresponding amines. The preparation of alkylguanidines is described, for example, in DE-C-506 282. In the process, alkylamines are guanidylated in an alcoholic solution with cyanamide in the presence of a protic acid. The products are obtained as crystalline salts. The preparation of the ether guanidines according to the invention can take place in an analogous manner by reacting ether amines in an alcoholic solution with cyanamide in the presence of a protic acid.

The preparation of the ether guanidines according to the invention can also take place by reacting the ether amines with other guanidylation agents as cyanamide. A list of further guanidylation agents and methods can be found, inter alia, in EP 1 462 463, Ullmann's Encyclopedia of Industrial Chemistry "Guanidine and Derivatives" chapter 2.4 or Houben-Weyl, E 4, 608-624.

The ether amines used according to the invention can be obtained in a simple manner by reacting corresponding alcohols $R^3$—OH, where $R^3$ has the meaning given above, with acrylonitrile according to the reaction scheme below:

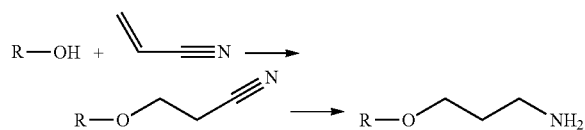

alcohol+acrylonitrile ether nitrile ether amine

A detailed description of the preparation of such ether amines can be found, for example, in EP 1 219 597.

Ether amines are commercially available products and are supplied, inter alia, by Tomah Products (USA) under the trade name Tomamine® and from Evonik Degussa GmbH under the trade name Adogen®.

The ether guanidines according to the invention can be used, for example, in hair treatment compositions and hair aftertreatment compositions. Within the context of the present invention, hair aftertreatment compositions are understood in particular as meaning those (cosmetic) preparations which are used for the aftertreatment, shaping and care of the hair following a chemical treatment of the hair (hair aftertreatment compositions). Within the context of the present invention, hair treatment compositions are understood as meaning in particular (chemical) hair treatment compositions through which the hair structure is damaged and in which the damage can be minimized through the addition of ether guanidines.

The hair aftertreatment compositions according to the invention may be, for example, hair rinses, hair treatments, reviving compositions, leave-in conditioners, hair shampoos, two-in-one-shampoos, setting formulations such as foam setting compositions, hair sprays or blow-waving lotions, hair tonics or hair end fluids. They may, for example, be in the form of a gel, emulsion, solution, aerosol spray or foam, nonaerosol spray or nonaerosol foam.

The hair treatment compositions and hair aftertreatment compositions according to the invention, in particular for preventing damage by chemical treatment compositions or exogenous factors, for repairing hair which is already damaged and for strengthening the hair are characterized in that they have one or more of the ether guanidines according to the invention as active substance. Preferably, the hair treatment compositions and hair aftertreatment compositions according to the invention comprise 0.01 to 10.0% by weight, preferably 0.05 to 8.0% by weight, preferably 0.1 to 5.0% by weight and particularly preferably 0.1 to 2.5% by weight of at least one of the ether guanidines according to the invention. Preferably, the specified weight fractions represent the fractions of all ether guanidines according to the invention in the compositions according to the invention.

As regards the way according to which the ether guanidines according to the invention and/or the hair treatment composition according to the invention is applied to the keratin fibres, in particular human hair, there are in principle no limitations. Suitable formulations of these preparations are, for example, creams, lotions, solutions, water, emulsions such as W/O, O/W, PIT emulsions (emulsions in accordance with the teaching of phase inversion, called PIT), microemulsions and multiple emulsions, gels, sprays, aerosols and foam aerosols.

The pH of the hair treatment composition according to the invention can preferably be values from 2 to 11, preferably values from 3 to 10. The hair treatment compositions and hair aftertreatment compositions according to the invention particularly preferably have a pH of from 3 to 7. Virtually any acid or base which can be used for cosmetic purposes and/or any buffer mixture can be used for adjusting the pH. Preferred bases are ammonia, alkali metal hydroxides, monoethanolamine, triethanolamine, and N,N,N',N'-tetrakis-(2-hydroxypropyl)ethylenediamine. Preferred acids are, for example, lactic acid or citric acid.

Hair treatment compositions and hair aftertreatment compositions according to the invention which remain on the hair have proven to be effective and can therefore constitute preferred embodiments of the teaching according to the invention. According to the invention, compositions which remain on the hair are to be understood as meaning those compositions which, in the course of the treatment, are not rinsed out of the hair again after a period of from a few seconds up to one hour with the help of water or an aqueous solution. Instead, the preparations remain on the hair until the next hair wash, i.e. usually more than 12 hours.

According to a second preferred embodiment, these preparations are formulated as hair treatment or hair conditioner. The hair treatment compositions and hair aftertreatment compositions according to the invention in accordance with these embodiments can, after this contact time has elapsed, be rinsed out with water or an at least predominantly water-containing composition; they may, however, as detailed above, be left on the hair.

According to further preferred embodiments, the compositions according to the invention may, however, for example also be cleaning compositions such as shampoos, care compositions such as rinses, setting compositions such as hair setting compositions, foam setting compositions, styling gels and blow-dry waves, permanent shaping compositions such as permanent waving compositions and neutralizing compositions, and also pretreatment compositions or afterrinses used in particular in the course of a permanent waving process or colouring process.

Besides the aforementioned ingredients obligatorily required and optional according to the invention, the preparations of this invention can in principle comprise all other components known to the person skilled in the art for such cosmetic compositions.

Further active ingredients, auxiliaries and additives are, for example, nonionic polymers, such as, for example, vinylpyrrolidone/vinyl acrylate copolymers, polyvinylpyrrolidone and vinylpyrrolidone/vinyl acetate copolymers and polysiloxanes, thickeners, such as agar-agar, guar gum, alginates, xanthan gum, gum arabic, karaya gum, carob seed flour, linseed gums, dextrans, cellulose derivatives, e.g. methylcellulose, hydroxy-alkylcellulose and carboxymethylcellulose, starch fractions and derivatives, such as amylose, amylopectin and dextrins, clays, such as, for example, bentonite or completely synthetic hydrocolloids, such as, for example, polyvinyl alcohol, hair-conditioning compounds, such as phospholipids, for example soya lecithin, egg lecithin and cephalins, and also silicone oils, perfume oils, dimethyl isosorbide and cyclodextrins, solvents and solubility promoters such as ethanol, isopropanol, ethylene glycol, propylene glycol, glycerol and diethylene glycol, symmetrical and asymmetrical, unbranched and branched dialkyl ethers having in total from 12 to 36 carbon atoms, in particular 12 to 24 carbon atoms, such as, for example, di-n-octyl ether, di-n-decyl ether, di-n-nonyl ether, di-n-undecyl ether and di-n-dodecyl ether, n-hexyl n-octyl ether, n-octyl n-decyl ether, n-decyl n-undecyl ether, n-undecyl n-dodecyl ether and n-hexyl n-undecyl ether, and di-tert-butyl ether, diisopentyl ether, di-3-ethyldecyl ether, tert-butyl n-octyl ether, isopentyl n-octyl ether and 2-methylpentyl n-octyl ether, fatty alcohols, in particular unbranched and/or saturated fatty alcohols having 8 to 30 carbon atoms, monoesters of C8 to C30-fatty acids with alcohols having 6 to 24 carbon atoms, fibre-structure-improving active ingredients, in particular mono-, di- and oligosaccharides, such as, for example, glucose, galactose, fructose, fruit sugar and lactose, conditioning active ingredients, such as paraffin oils, vegetable oils, e.g. sunflower oil, orange oil, almond oil, wheat germ oil and peach kernel oil, and also phospholipids, for example soya lecithin, egg lecithin and cephalins, quaternized amines, such as methyl-1-alkylamidoethyl-2-alkylimidazolinium methosulphate, antifoams such as silicones, dyes for colouring the composition, antidandruff active ingredients, such as piroctone olamine, zinc omadine and climbazole, active ingredients such as allantoin and bisabolol, cholesterol, consistency regulators, such as sugar esters, polyol esters or polyol alkyl ethers, fats and waxes, such as spermaceti, beeswax, montan wax and paraffins, fatty acid alkanolamides, complexing agents, such as EDTA, NTA, alanine diacetic acid and phosphonic acids, swelling and penetration substances, such as primary, secondary and tertiary phosphates, opacifiers, such as latex, styrene/PVP- and styrene/acrylamide copolymers, pearlizing agents, such as ethylene glycol mono- and distearate, and also PEG-3 distearate, pigments, reducing agents, such as, for example, thioglycolic acid and derivatives thereof, thiolactic acid, cysteamine, thiomalic acid and thiomercaptoethanesulphonic acid, propellants, such as propane/butane mixtures, $N_2O$, dimethyl ether, $CO_2$ and air, antioxidants.

As regards further optional components and also the amounts of these components used, reference is made expressly to the relevant handbooks known to the person skilled in the art, e.g. K. Schrader, "Grundlagen and Rezepturen der Kosmetika [Fundamentals and formulations of cosmetics]", $2^{nd}$ edition, page 329 to 341, Hüthig Buch Verlag Heidelberg.

The hair treatment compositions and hair aftertreatment compositions according to the invention which have the ether guanidines according to the invention can moreover comprise from 0 to 10% by weight, preferably from 0.1 to 7.5% by weight, of one or more emulsifiers, from 0 to 10% by weight, preferably from 0.1 to 7.5% by weight, of one or more consistency regulators, from 0 to 10% by weight, preferably from 0.1 to 7.5% by weight, of one or more, preferably cationic, surfactants and/or polymers with one or more quaternary ammonium groups and/or from 0 to 20% by weight, preferably from 0.1 to 17.5% by weight, of one or more cosmetic oils or emollients, and optionally customary auxiliaries and additives in customary concentrations. The remainder can be, for example, water (ad 100% by weight water).

Besides the specified compounds, the hair treatment compositions and hair aftertreatment compositions according to the invention can comprise one or more hair cosmetic active ingredients, preferably selected from the group of protein hydrolysates of vegetable or animal origin based on keratin, collagen, elastin, peas, wheat, rice, soya, milk, silk or corn, antidandruff active ingredients, such as, for example, piroctone olamine, zinc omadine, pyrithione derivatives (e.g. zinc pyrithione, aluminium pyrithione), sulphur colloidal, salicylic acid derivatives, selenium disulphide, selenium oxide, bifonazole, actirox and climbazole, sebostatics, vitamins and/or vitamin precursors and/or derivatives of vitamins or vitamin precursors, panthenol, pyrrolidonecarboxylic acid, bisabolol, plant extracts, niacinamide, polymeric quats, silicone compounds, creatine and/or ceramides.

Vitamins, provitamins and vitamin precursors preferred according to the invention are those which are usually assigned to the groups A, B, C, E, F and H.

The group of substances referred to as vitamin A includes, for example, retinol (vitamin A1) and 3,4-didehydroretinol (vitamin A2). β-Carotene is the provitamin of retinols. According to the invention, suitable vitamin A components are, for example, vitamin A acid and esters thereof, vitamin A aldehyde and vitamin A alcohol, and also esters thereof, such as the palmitate and the acetate. The preparations used according to the invention comprise the vitamin A component preferably in amounts of from 0.05-1% by weight, based on the total preparation.

The vitamin B group or the vitamin B complex includes, inter alia, vitamin B1 (thiamine), vitamin B2 (riboflavin) and vitamin B3. This term often includes the compounds nicotinic acid and nicotinamide (niacinamide). According to the invention, preference is given to nicotinamide, which is present in the compositions used according to the invention preferably in amounts of from 0.05 to 1% by weight, based on the total composition. The vitamin B group or the vitamin B complex also includes Vitamin B5 (pantothenic acid, panthenol and pantolactone). Within this group, preference is given to using panthenol and/or pantolactone. Derivatives of panthenol which can be used according to the invention are, in particular, the esters and ethers of panthenol and cationically derivatized panthenols. Individual representatives are, for example, panthenol triacetate, panthenol monoethyl ether and its monoacetate, and also the cationic panthenol derivatives disclosed in WO 92/13829. The specified compounds of the vitamin B5 type are present in the compositions used according to the invention preferably in amounts of 0.05-10% by weight, based on the total composition. Amounts of 0.1-5% by weight are particularly preferred. The vitamin B group or the vitamin B complex includes Vitamin B6 (pyridoxine and also pyridoxamine and pyridoxal).

Vitamin C (ascorbic acid) is used in the compositions used according to the invention preferably in amounts of from 0.1 to 3% by weight, based on the total composition. The use in the form of the palmitic acid ester, the glucosides or phosphates may be preferred. The use in combination with tocopherols may likewise be preferred.

Vitamin E (tocopherols, in particular α-tocopherol). Tocopherol and its derivatives, which include in particular the esters, such as the acetate, the nicotinate, the phosphate and the succinate, are present in the compositions used according to the invention preferably in amounts of 0.05-1% by weight, based on the total composition.

Vitamin F. The term "vitamin F" is usually understood as meaning essential fatty acids, in particular linoleic acid, linolenic acid and arachidonic acid.

Vitamin H is the term used to refer to the compound (3aS, 4S,6aR)-2-oxohexahydrothienol[3,4-d]-imidazole-4-valeric acid, although the trivial name biotin has caught on in the meantime. Biotin is present in the compositions used according to the invention preferably in amounts of from 0.0001 to 1.0% by weight, in particular in amounts of from 0.001 to 0.01% by weight.

Preferably, the compositions used according to the invention comprise vitamins, provitamins and vitamin precursors from groups A, B, E and H. Panthenol, pantolactone, pyridoxine and its derivatives and also nicotinamide and biotin are particularly preferred.

Plant extracts suitable according to the invention are preferably prepared by extraction of the whole plant. However, in individual cases, it may also be preferred to prepare the extracts exclusively from flowers and/or leaves of the plant.

With regard to the plant extracts which can be used according to the invention, reference is made in particular to the extracts which are listed in the table starting on page 44 of the $3^{rd}$ edition of the Introduction to the Ingredients Declaration of Cosmetic Compositions, published by the Industrieverband Körperpflege- and Waschmittel e.V. (IKW), Frankfurt.

According to the invention, especially the extracts from green tea, oak bark, stinging nettle, hamamelis, hops, henna, camomile, burdock, horsetail, hawthorn, linden blossom, almond, aloe vera, fir needle, horse chestnut, sandalwood, juniper, coconut, mango, apricot, lime, wheat, kiwi, melon, orange, grapefruit, sage, rosemary, birch, mallow, lady's smock, wild thyme, yarrow, thyme, melissa, restharrow, coltsfoot, marshmallow, meristem, ginseng and ginger root are preferred. Particular preference is given to the extracts from green tea, oak bark, stinging nettle, hamamelis, hops, camomile, burdock, horsetail, linden blossom, almond, aloe vera, coconut, mango, apricot, lime, wheat, kiwi, melon, orange, grapefruit, sage, rosemary, birch, lady's smock, wild thyme, yarrow, restharrow, meristem, ginseng and ginger root. Of very particular suitability for the use in hair treatment compositions and hair aftertreatment compositions according to the invention are the extracts from green tea, almond, aloe vera, coconut, mango, apricot, lime, wheat, kiwi and melon.

Extractants which can be used for preparing the specified plant extracts are, for example, water, alcohols and mixtures thereof. In this connection, among the alcohols, lower alcohols such as ethanol and isopropanol, but in particular polyhydric alcohols, such as ethylene glycol and propylene glycol, either as the sole extractant or else in a mixture with water, are preferred. Plant extracts based on water/propylene glycol in the ratio 1:10 to 10:1 have proven to be particularly suitable.

According to the invention, the plant extracts can be used either in pure form or in diluted form. If they are used in diluted form, they usually comprise ca. 2-80% by weight of active substance and, as solvent, preferably the extractant or extractant mixtures used in their recovery.

Furthermore, it may be preferred to use mixtures of two or more, in particular of two, different plant extracts in the compositions according to the invention.

Protein hydrolysates suitable according to the invention are, for example, product mixtures which are obtained by acidically, basically or enzymatically catalyzed degradation of proteins. According to the invention, the term protein hydrolysates is also to be understood as meaning total hydrolysates, as well as individual amino acids and derivatives thereof, and also mixtures of different amino acids. Furthermore, according to the invention, polymers constructed from amino acids and amino acid derivatives are understood by the term protein hydrolysates. The latter include, for example, polyalanine, polyasparagine, polyserine, polyglutamic acid etc. Further examples of compounds which can be used according to the invention are L-alanyl-L-proline, polyglycine, glycyl-L-glutamine or D/L-methionine-S-methylsulphonium chloride. According to the invention, it is also of course possible to use β-amino acids and derivatives thereof such as β-alanine, anthranilic acid or hippuric acid. The molecular weight of the protein hydrolysates which can be used according to the invention is preferably from 75, the molecular weight for glycine, to 200 000, preferably the molecular weight is 75 to 50 000 and very particularly preferably 75 to 20 000 daltons.

According to the invention, protein hydrolysates both of vegetable origin, and also of animal or marine or synthetic origin may be used.

Animal protein hydrolysates are, for example, the protein hydrolysates of elastin, collagen, keratin and milk protein, which may also be present in the form of salts. Such products are sold, for example, under the trade names Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex) and Kerasol® (Croda).

According to the invention, the use of protein hydrolysates of vegetable origin, e.g. soya, almond, pea, potato and wheat protein hydrolysates, is preferred. Such products are obtainable, for example, under the trade names Gluadin® (Cognis), DiaMin® (Diamalt), Lexein®(Inolex), Hydrosoy® (Croda), Hydrolupin® (Croda), Hydrosesame® (Croda), Hydrotritium (Croda) and Crotein®(Croda).

Although the use of the protein hydrolysates as such is preferred, instead of them it is in some cases also possible to use amino acid mixtures obtained in other ways. It is likewise possible to use derivatives of protein hydrolysates, for example in the form of their fatty acid condensation products. Such products are sold, for example, under the names Lamepon® (Cognis), Lexein® (Inolex), Crolastin® (Croda) or Crotein® (Croda).

The teaching according to the invention of course encompasses all isomeric forms, such as cis-trans isomers, diastereomers and chiral isomers. According to the invention, it is also possible to use a mixture of two or more protein hydrolysates.

The protein hydrolysates are present in the compositions according to the invention preferably in concentrations of from 0.01% by weight up to 20% by weight, preferably from 0.05% by weight up to 15% by weight and very particularly preferably in amounts of from 0.05% by weight up to 5% by weight.

Silicone oils suitable according to the invention bring about highly diverse effects. Thus, for example, they are able to simultaneously influence the dry and wet combabilities, the feel of the dry and wet hair and also the shine. The term silicone oils is understood by the person skilled in the art as meaning several structures of organosilicon compounds. Firstly, this is to be understood as meaning the dimethiconols (S1).

Dimethiconols form the first group of silicones which are particularly preferred according to the invention. The dimethiconols according to the invention may either be unbranched or branched or else cyclic or cyclic and branched. Unbranched dimethiconols can be represented by the following structural formula (S1-1):

$$(SiOHR^1{}_2)-O-(SiR^2{}_2-O-)_x-(SiOHR^1{}_2) \qquad (S1\text{-}1)$$

Branched dimethiconols can be represented by the structural formula (S1-2):

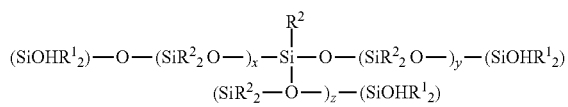

(S1-2)

The radicals $R^1$ and $R^2$, independently of one another, are in each case hydrogen, a methyl radical, a $C_2$ to $C_{30}$ unbranched, saturated or unsaturated hydrocarbon radical, a phenyl radical and/or an aryl radical. Nonlimiting examples of the radicals represented by $R^1$ and $R^2$ include alkyl radicals, such as methyl, ethyl, propyl, isopropyl, butyl, isobutyl, pentyl, isopentyl, neopentyl, amyl, isoamyl, hexyl, isohexyl and the like; alkenyl radicals, such as vinyl, halovinyl, alkylvinyl, allyl, haloallyl, alkylallyl; cycloalkyl radicals, such as cyclobutyl, cyclopentyl, cyclohexyl and the like; phenyl radicals, benzyl radicals, halohydrocarbon radicals, such as 3-chloropropyl, 4-bromobutyl, 3,3,3-trifluoropropyl, chlorocyclohexyl, bromophenyl, chlorophenyl and the like, and also sulphur-containing radicals, such as mercaptoethyl, mercaptopropyl, mercaptohexyl, mercapto-phenyl and the like; preferably, $R^1$ and $R^2$ is an alkyl radical, which comprises 1 to about 6 carbon atoms. Preferably, $R^1$ and $R^2$ is methyl. Examples of $R^1$ include methylene, ethylene, propylene, hexamethylene, decamethylene, $-CH_2CH(CH_3)CH_2-$, phenylene, naphthylene, $-CH_2CH_2SCH_2CH_2-$, $-CH_2CH_2OCH_2-$, $-OCH_2CH_2-$, $-OCH_2CH_2CH_2-$, $-CH_2CH(CH_3)C(O)OCH_2-$, $-(CH_2)_3CC(O)OCH_2CH_2-$, $-C_6H_4C_6H_4-$, $-C_6H_4CH_2C_6H_4-$; and $-(CH_2)_3C(O)SCH_2CH_2-$. Preferred $R^1$ and $R^2$ are methyl, phenyl and $C_2$ to $C_{22}$-alkyl radicals. The $C_2$ to $C_{22}$ alkyl radicals are very particularly preferably lauryl, stearyl and behenyl radicals. The numbers x, y and z are integers and run, in each case independently of one another, from 0 to 50 000. The molecular weights of the dimethicones are preferably between 1000 D and 10 000 000 D. The viscosities are preferably between 100 and 10 000 000 cPs measured at 25° C. with the help of a glass capillary viscometer according to the Dow Corning Corporate Test Method CTM 0004 of 20 Jul. 1970. Preferred viscosities are between 1000 and 5 000 000 cPs, particularly preferred viscosities are between 10 000 and 3 000 000 cPs and very particularly preferably between 50 000 and 2 000 000 cPs.

The teaching according to the invention of course also encompasses the fact that the dimethiconols may already be present as emulsion. The corresponding emulsion of the dimethiconols can be prepared according to the preparation of the corresponding dimethiconols either by these processes or by the customary processes for emulsification known to the person skilled in the art. For this, auxiliaries which can be used for the preparation of the corresponding emulsions are either cationic, anionic, nonionic or zwitterionic surfactants and emulsifiers. The emulsions of the dimethiconols can of course also be prepared directly by an emulsion polymerization process. Processes of this type are also well known to the person skilled in the art. In this regard, reference may be made, for example, to the "Encyclopedia of Polymer Science and Engineering, Volume 15, Second Edition, pages 204 to 308, John Wiley & Sons, Inc. 1989". Reference is expressly made to this standard work.

If the dimethiconols according to the invention are used as emulsion, then the droplet size of the emulsified particles is preferably 0.01 μm to 10 000 μm, preferably 0.01 to 100 μm, particularly preferably 0.01 to 20 μm and very particularly preferably 0.01 to 10 μm. The particle size here is determined according to the light-scattering method.

If branched dimethiconols are used, then this term is to be understood as meaning that branching is greater than coincident branching which arises by chance as a result of impurities of the particular monomers. Within the context of the present compound, branched dimethiconols are therefore to be understood as meaning those where the degree of branching is greater than 0.01%. Preference is given to a degree of branching greater than 0.1% and very particularly preferably greater than 0.5%. The degree of branching here is determined from the ratio of the branched monomers, i.e. the amount of monofunctional siloxane, to the branching monomers, i.e. the amount of tri- and tetrafunctional siloxanes. According to the invention, dimethiconols both with a low degree of branching and also with a high degree of branching may be preferred.

The following commercial products are specified as examples of such products: Botanisil NU-150M (Botanigenics), Dow Corning 1-1254 Fluid, Dow Corning 2-9023 Fluid, Dow Corning 2-9026 Fluid, Ultrapure Dimethiconol (Ultra Chemical), Unisil SF-R (Universal Preserve), X-21-5619 (Shin-Etsu Chemical Co.), Abil® OSW 5 (Degussa Care Specialties), ACC DL-9430 Emulsion (Taylor Chemical Company), AEC Dimethiconol & Sodium Dodecylbenzenesulphonate (A & E Connock (Perfumery & Cosmetics) Ltd.), B C Dimethiconol Emulsion 95 (Basildon Chemical Company, Ltd.), Cosmetic Fluid 1401, Cosmetic Fluid 1403, Cosmetic Fluid 1501, Cosmetic Fluid 1401DC (alle zuvor genannten Chemsil Silicones, Inc.), Dow Corning 1401 Fluid, Dow Corning 1403 Fluid, Dow Corning 1501 Fluid, Dow Corning 1784 HVF Emulsion, Dow Corning 9546 Silicone Elastomer Blend (alle zuvor genannten Dow Corning Corporation), Dub Gel SI 1400 (Stearinerie Dubois Fils), HVM 4852 Emulsion (Crompton Corporation), Jeesile 6056 (teen International Corporation), Lubrasil, Lubrasil DS (beide Guardian Laboratories), Nonychosine E, Nonychosine V (beide Exsymol), SanSurf Petrolatum-25, Satin Finish (beide Collaborative Laboratories, Inc.), Silatex-D30 (Cosmetic Ingredient Resources), Silsoft 148, Silsoft E-50, Silsoft E-623 (alle zuvor genannten Crompton Corporation), SM555, SM2725, SM2765, SM2785 (alle zuvor genannten GE Silicones), Taylor T-Sil CD-1, Taylor TME-4050E (alle Taylor Chemical Company), TH V 148 (Crompton Corporation), Tixogel CYD-1429 (Sud-Chemie Performance Additives), Wacker-Belsil CM 1000, Wacker-Belsil CM 3092, Wacker-Belsil CM 5040, Wacker-Belsil DM 3096, Wacker-Belsil DM 3112 VP, Wacker-Belsil DM 8005 VP, Wacker-Belsil DM 60081 VP (all of the aforementioned Wacker-Chemie GmbH).

If the dimethiconols (S1) are present in the hair treatment compositions and hair aftertreatment compositions according to the invention, then these comprise preferably 0.01 to 10% by weight, preferably 0.1 to 8% by weight, particularly preferably 0.25 to 7.5% by weight and in particular 0.5 to 5% by weight, of dimethiconol, based on the total composition of the composition.

Dimethicones (S2) form the second group of silicones which are particularly preferred according to the invention. The dimethicones according to the invention may either be unbranched or branched and also cyclic or cyclic and branched. Unbranched dimethicones can be represented by the following structural formula (S2-1):

(S2-1)

Branched dimethicones can be represented by the structural formula (S2-2):

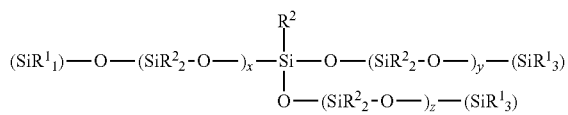

(S2-2)

The radicals $R^1$ and $R^2$, independently of one another, are in each case hydrogen, a methyl radical, a $C_2$ to $C_{30}$ unbranched, saturated or unsaturated hydrocarbon radical, a phenyl radical and/or an aryl radical. Nonlimiting examples of the radicals represented by $R^1$ and $R^2$ include alkyl radicals, such as methyl, ethyl, propyl, isopropyl, butyl, isobutyl, pentyl, isopentyl, neopentyl, amyl, isoamyl, hexyl, isohexyl and the like; alkenyl radicals, such as vinyl, halovinyl, alkylvinyl, allyl, haloallyl, alkylallyl; cycloalkyl radicals, such as cyclobutyl, cyclopentyl, cyclohexyl and the like; phenyl radicals, benzyl radicals, halohydrocarbon radicals, such as 3-chloropropyl, 4-bromobutyl, 3,3,3-trifluoropropyl, chlorocyclohexyl, bromophenyl, chlorophenyl and the like, and also sulphur-containing radicals, such as mercaptoethyl, mercaptopropyl, mercaptohexyl, mercapto-phenyl and the like; preferably, $R^1$ and $R^2$ is an alkyl radical which contains 1 to about 6 carbon atoms, and most preferably $R^1$ and $R^2$ is methyl. Examples of $R^1$ include methylene, ethylene, propylene, hexamethylene, decamethylene, —$CH_2CH(CH_3)CH_2$—, phenylene, naphthylene, —$CH_2CH_2SCH_2CH_2$—, —$CH_2CH_2OCH_2$—, —$OCH_2CH_2$—, —$OCH_2CH_2CH_2$—, —$CH_2CH(CH_3)C(O)OCH_2$—, —$(CH_2)_3CC(O)OCH_2CH_2$—, —$C_6H_4C_6H_4$—, —$C_6H_4CH_2C_6H_4$—; and —$(CH_2)_3C(O)SCH_2CH_2$—. Preferably, $R^1$ and $R^2$ are methyl, phenyl and $C_2$- to $C_{22}$-alkyl radicals. The $C_2$- to $C_{22}$-alkyl radicals are very particularly preferably lauryl, stearyl and behenyl radicals. The numbers x, y and z are integers and run, in each case independently of one another, from 0 to 50 000. The molecular weights of the dimethicones are preferably between 1000 D and 10 000 000 D. The viscosities are preferably between 100 and 10 000 000 cPs measured at 25 degrees C. with the help of a glass capillary viscometer according to the Dow Corning Corporate Test Method CTM 0004 of 20 Jul. 1970. Particularly preferred viscosities are between 1000 and 5 000 000 cPs, very particularly preferred viscosities are between 10 000 and 3 000 000 cPs. The most preferred range is between 50 000 and 2 000 000 cPs.

The teaching according to the invention of course also encompasses the fact that the dimethicones may already be present as emulsion. Here, the corresponding emulsion of the dimethicones can be prepared according to the preparation of the corresponding dimethicones either by these processes or by the customary processes for emulsification known to the person skilled in the art. For this, auxiliaries which can be used for the preparation of the corresponding emulsions are either cationic, anionic, nonionic or zwitterionic surfactants and emulsifiers. The emulsions of the dimethicones can of course also be prepared directly by an emulsion polymerization process. Processes of this type are also well known to the person skilled in the art. In this regard, reference may be made, for example, to the "Encyclopedia of Polymer Science and Engineering, Volume 15, Second Edition, pages 204 to 308, John Wiley & Sons, Inc. 1989." Reference is made expressly to this standard work.

If the dimethicones according to the invention are used as emulsion, then the droplet size of the emulsified particles is, according to the invention, 0.01 μm to 10 000 μm, preferably 0.01 to 100 μm, very particularly preferably 0.01 to 20 μm and most preferably 0.01 to 10 μm. The particle size here is determined by the light-scattering method.

If branched dimethicones are used, then this term is to be understood as meaning that the branching is greater than coincidental branching which arises by chance as a result of impurities of the particular monomers. Within the context of the present compound, branched dimethicones are therefore to be understood as meaning those where the degree of branching is greater than 0.01%. Preference is given to a degree of branching greater than 0.1% and very particularly preferably greater than 0.5%. The degree of branching here is determined from the ratio of the unbranched monomers, i.e. the amount of monofunctional siloxane, to the branching monomers, i.e. the amount of tri- and tetrafunctional siloxanes. According to the invention, dimethicones with both a low degree of branching and also a high degree of branching may be very particularly preferred.

If the dimethicones (S2) are present in the hair treatment compositions and hair aftertreatment compositions according to the invention, then these compositions comprise preferably 0.01 to 10% by weight, preferably 0.1 to 8% by weight, particularly preferably 0.25 to 7.5% by weight and in particular 0.5 to 5% by weight, of dimethiconol, based on the total composition.

Dimethicone copolyols (S3) form a further group of preferred silicones. Dimethicone copolyols can be represented by the following structural formulae:

         (S3-1)

or by the following structural formula:

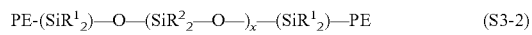         (S3-2)

Branched dimethicone copolyols can be represented by the structural formulae (S3-3) or (S3-4):

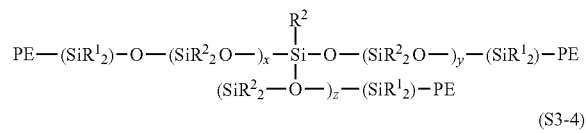

(S3-3)

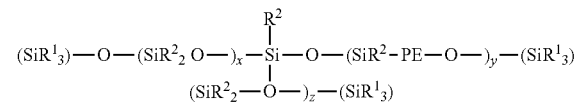

(S3-4)

The radicals $R^1$ and $R^2$, independently of one another, are in each case hydrogen, a methyl radical, a $C_2$ to $C_{30}$ unbranched, saturated or unsaturated hydrocarbon radical, a phenyl radical and/or an aryl radical. Nonlimiting examples of the radicals represented by $R^1$ and $R^2$ include alkyl radicals, such as methyl, ethyl, propyl, isopropyl, butyl, isobutyl, pentyl, isopentyl, neopentyl, amyl, isoamyl, hexyl, isohexyl and the like; alkenyl radicals, such as vinyl, halovinyl, alkylvinyl, allyl, haloallyl, alkylallyl; cycloalkyl radicals, such as cyclobutyl, cyclopentyl, cyclohexyl and the like; phenyl radicals, benzyl radicals, halohydrocarbon radicals, such as 3-chloropropyl, 4-bromobutyl, 3,3,3-trifluoropropyl, chlorocyclohexyl, bromophenyl, chlorophenyl and the like, and also sulphur-containing radicals, such as mercaptoethyl, mercaptopropyl, mercaptohexyl, mercapto-phenyl and the like; preferably, $R^1$ and $R^2$ is an alkyl radical which contains 1 to about 6 carbon atoms, and most preferably $R^1$ and $R^2$ is methyl. Examples of $R^1$ include methylene, ethylene, propylene, hexamethylene, decamethylene, —CH$_2$CH(CH$_3$)CH$_2$—, phenylene, naphthylene, —CH$_2$CH$_2$SCH$_2$CH$_2$—, —CH$_2$CH$_2$OCH$_2$—, —OCH$_2$CH$_2$—, —OCH$_2$CH$_2$CH$_2$—, —CH$_2$CH(CH$_3$)C(O)OCH$_2$—, —(CH$_2$)$_3$CC(O)OCH$_2$CH$_2$—, —C$_6$H$_4$C$_6$H$_4$—, —C$_6$H$_4$CH$_2$C$_6$H$_4$—; and —(CH$_2$)$_3$C(O)SCH$_2$CH$_2$—. Preferably, R$^1$ and R$^2$ are methyl, phenyl and C$_2$- to C$_{22}$-alkyl radicals. The C$_2$- to C$_{22}$-alkyl radicals are very particularly preferably lauryl, stearyl and behenyl radicals. PE stands for a polyoxyalkylene radical. Preferred polyoxyalkylene radicals are derived from ethylene oxide, propylene oxide and glycerol. The numbers x, y and z are integers and run preferably in each case independently of one another from to 50 000. The molecular weights of the dimethicone copolyols are between 1000 D and 10 000 000 D. The viscosities are between 100 and 10 000 000 cPs measured at 25 degrees C. with the help of a glass capillary viscometer according to the Dow Corning Corporate Test Method CTM 0004 from 20 Jul. 1970. Preferred viscosities are between 1000 and 5 000 000 cPs, very particularly preferred viscosities are between 10 000 and 3 000 000 cPs. The most preferred range is between 50 000 and 2 000 000 cPs.

The teaching according to the invention also of course encompasses the fact that the dimethicone copolymers may already be present as emulsion. In this connection, the corresponding emulsion of the dimethicone copolyols can be prepared according to the preparation of the corresponding dimethicone copolyols either by these processes or by the customary processes for emulsification known to the person skilled in the art. For this purpose, auxiliaries which can be used for preparing the corresponding emulsions are cationic, anionic, nonionic or zwitterionic surfactants and emulsifiers. The emulsions of the dimethicone copolyols can of course also be prepared directly by an emulsion polymerization process. Processes of this type are also well known to the person skilled in the art. In this regard, reference may be made, for example, to the "Encyclopedia of Polymer Science and Engineering, Volume 15, Second Edition, pages 204 to 308, John Wiley & Sons, Inc. 1989". Reference is expressly made to this standard work.

If the dimethicone copolyols according to the invention are used as emulsion, then the droplet size of the emulsified particles is, according to the invention, preferably from 0.01 µm to 10 000 µm, preferably 0.01 to 100 µm, very particularly preferably 0.01 to 20 µm and most preferably 0.01 to 10 µm. The particle size here is determined according to the light-scattering method.

If branched dimethicone copolyols are used, then this term is to be understood as meaning that the branching is greater than coincidental branching which arises by chance as a result of impurities of the particular monomers. Within the context of the present compound, branched dimethicone copolyols are therefore to be understood as meaning those where the degree of branching is greater than 0.01%. Preference is given to a degree of branching greater than 0.1% and very particularly preferably greater than 0.5%. The degree of branching here is determined from the ratio of the unbranched monomers, i.e. the amount of monofunctional siloxane, to the branching monomers, i.e. the amount of tri- and tetrafunctional siloxanes. According to the invention, dimethicone copolyols both with a low degree of branching and also with a high degree of branching may be very particularly preferred.

If the dimethicone copolyols (S3) are present in the hair treatment compositions and hair aftertreatment compositions according to the invention, then these comprise from 0.01 to 10% by weight, preferably 0.1 to 8% by weight, particularly preferably 0.25 to 7.5% by weight and in particular 0.5 to 5% by weight, of dimethicone copolyol, based on the total composition.

Aminofunctional silicones, also called amodimethicones (S4), are silicones which have at least one (optionally substituted) amino group.

Such silicones can be described, for example, by the formula (S4-1)

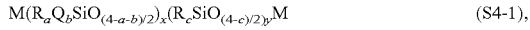

$$M(R_aQ_bSiO_{(4-a-b)/2})_x(R_cSiO_{(4-c)/2})_yM \qquad (S4\text{-}1),$$

where, in the above formula, R is a hydrocarbon or a hydrocarbon radical having 1 to about 6 carbon atoms, Q is a polar radical of the general formula —R$^1$HZ, in which R$^1$ is a divalent, joining group which is bonded to hydrogen and the radical Z, composed of carbon and hydrogen atoms, carbon, hydrogen and oxygen atoms or carbon, hydrogen and nitrogen atoms, and Z is an organic, aminofunctional radical which contains at least one aminofunctional group; "a" assumes values in the range from about 0 to about 2, "b" assumes values in the range from about 1 to about 3, "a"+"b" is less than or equal to 3, and "c" is a number in the range from about 1 to about 3, and x is a number in the range from 1 to about 2000, preferably from about 3 to about 50 and most preferably from about 3 to about 25, and y is a number in the range from about 20 to about 10 000, preferably from about 125 to about 10 000 and most preferably from about 150 to about 1000, and M is a suitable silicone end group, as is known in the prior art, preferably trimethylsiloxy. Nonlimiting examples of the radicals represented by R include alkyl radicals, such as methyl, ethyl, propyl, isopropyl, butyl, isobutyl, amyl, isoamyl, hexyl, isohexyl and the like; alkenyl radicals, such as vinyl, halovinyl, alkylvinyl, allyl, haloallyl, alkylallyl; cycloalkyl radicals, such as cyclobutyl, cyclopentyl, cyclohexyl and the like; phenyl radicals, benzyl radicals, halohydrocarbon radicals, such as 3-chloropropyl, 4-bromobutyl, 3,3,3-trifluoropropyl, chlorocyclohexyl, bromophenyl, chlorophenyl and the like, and also sulphur-containing radicals, such as mercaptoethyl, mercaptopropyl, mercaptohexyl, mercapto-phenyl and the like; preferably, R is an alkyl radical which contains 1 to about 6 carbon atoms, and most preferably R is methyl. Examples of R and R$^1$ include methylene, ethylene, propylene, hexamethylene, decamethylene, —CH$_2$CH(CH$_3$)CH$_2$—, phenylene, naphthylene, —CH$_2$CH$_2$SCH$_2$CH$_2$—, —CH$_2$CH$_2$OCH$_2$—, —OCH$_2$CH$_2$—, —OCH$_2$CH$_2$CH$_2$—, —CH$_2$CH(CH$_3$)C(O)OCH$_2$—, —(CH$_2$)$_3$CC(O)OCH$_2$CH$_2$—, —C$_6$H$_4$C$_6$H$_4$—, —C$_6$H$_4$CH$_2$C$_6$H$_4$—; and —(CH$_2$)$_3$C(O)SCH$_2$CH$_2$—.

Z is an organic, aminofunctional radical comprising at least one functional amino group. One possible formula for Z is NH(CH$_2$)$_z$NH$_2$, in which z=1 or more. Another possible formula for Z is —NH(CH$_2$)$_z$(CH$_2$)$_{zz}$NH$_2$, in which both z and also zz, independently, are 1 or more, this structure including diamino ring structures such as piperazinyl. Z is most preferably a —NHCH$_2$CH$_2$NH$_2$— radical.

Another possible formula for Z is —N(CH$_2$)$_z$(CH$_2$)$_{zz}$NX$_2$ or —NX$_2$, in which each X in X$_2$ is selected independently from the group consisting of hydrogen and alkyl groups having 1 to 12 carbon atoms, and z is 0.

Q is most preferably a polar, aminofunctional radical of the formula —CH$_2$CH$_2$CH$_2$NHCH$_2$CH$_2$NH$_2$. In the formulae, "a" assumes values in the range from about 0 to about 2, "b" assumes values in the range from about 2 to about 3, "a"+"b" is less than or equal to 3, and "c" is a number in the range from about 1 to about 3. The molar ratio of the R$_a$Q$_b$SiO$_{(4-a-b)/2}$ units to the R$_c$SiO$_{(4-c)/2}$ units is preferably in the range from about 1:2 to 1:65, preferably from about 1:5 to about 1:65 and particularly preferably from about 1:15 to about 1:20. If one or more silicones of the above formula are used, then the various variable substituents in the above formula can be different for the different silicone components which are present in the silicone mixture.

Preferred compositions according to the invention are characterized in that they comprise an aminofunctional silicone of the formula (S4-2)

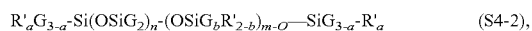

in which: G is —H, a phenyl group, —OH, —O—CH$_3$, —CH$_3$, —CH$_2$CH$_3$, —CH$_2$CH$_2$CH$_3$, —CH(CH$_3$)$_2$, —CH$_2$CH$_2$CH$_2$H$_3$, —CH$_2$CH(CH$_3$)$_2$, —CH(CH$_3$)CH$_2$CH$_3$, —C(CH$_3$)$_3$; a is a number from 0 to 3, in particular 0; b is a number from 0 to 1, in particular 1, m and n are numbers whose sum (m+n) is from 1 to 2000, preferably between 50 and 150, where n preferably assumes values from 0 to 1999 and in particular from 49 to 149 and m preferably assumes values from 1 to 2000, in particular from 1 to 10, R' is a monovalent radical selected from
  —N(R")—CH$_2$—CH$_2$—N(R")$_2$
  —N(R")$_2$
  —N$^+$(R")$_3$A$^-$
  —N$^+$H(R")$_2$A$^-$
  —N$^+$H$_2$(R")A$^-$
  —N(R")—CH$_2$—CH$_2$—N$^+$R"H$_2$A$^-$,
where each R" is identical or different radicals from the group —H, -phenyl, -benzyl, the C$_{1-20}$-alkyl radicals, preferably —CH$_3$, —CH$_2$CH$_3$, —CH$_2$CH$_2$CH$_3$, —CH(CH$_3$)$_2$, —CH$_2$CH$_2$CH$_2$H$_3$, —CH$_2$CH(CH$_3$)$_2$, —CH(CH$_3$)CH$_2$CH$_3$, —C(CH$_3$)$_3$, and A represents an anion which is preferably selected from chloride, bromide, iodide or methosulphate.

Particularly preferred compositions according to the invention are characterized in that they comprise an aminofunctional silicone of the formula (S4-3)

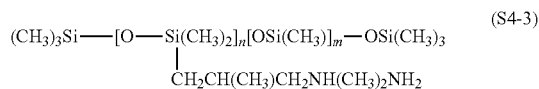

in which m and n are numbers whose sum (m+n) is from 1 to 2000, preferably between 50 and 150, where n preferably assumes values from 0 to 1999 and in particular from 49 to 149 and m preferably assumes values from 1 to 2000, in particular from 1 to 10. These silicones are referred to in accordance with the INCI Declaration as trimethylsilylamodimethicones.

Particular preference is also given to compositions according to the invention which are characterized in that they comprise an aminofunctional silicone of the formula (S4-4)

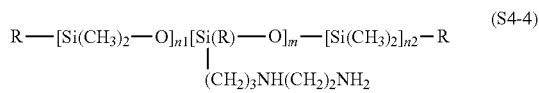

in which R is —OH, —O—CH$_3$ or a —CH$_3$ group and m, n1 and n2 are numbers whose sum (m+n1+n2) is from 1 to 2000, preferably between 50 and 150, where the sum (n1+n2) preferably assumes values from 0 to 1999 and in particular from 49 to 149 and m preferably assumes values from 1 to 2000, in particular from 1 to 10. These silicones are referred to in accordance with the INCI Declaration as amodimethicones (S4).

Irrespective of which aminofunctional silicones are used, preference is given to compositions according to the invention in which the aminofunctional silicone has an amine number above 0.25 meq/g, preferably above 0.3 meq/g and in particular above 0.4 meq/g. The amine number here is the milli-equivalents of amine per gram of the aminofunctional silicone. It can be determined by titration and also quoted in the unit mg KOH/g.

If the amodimethicones (S4) are present in the hair treatment compositions and hair aftertreatment compositions according to the invention, then these compositions comprise 0.01 to 10% by weight, preferably 0.1 to 8% by weight, particularly preferably 0.25 to 7.5% by weight and in particular 0.5 to 5% by weight, of amodimethicone, based on the total composition.

The invention also of course encompasses the finding that a mixture of at least two different silicones can be used in the hair treatment compositions and hair aftertreatment compositions according to the invention. Preferred mixtures of different silicones are, for example, dimethicones and dimethiconols, unbranched dimethicones and cyclic dimethiconols. A very particularly preferred mixtures of silicones consists of at least one cyclic dimethiconol and/or dimethicone, at least one further noncyclic dimethicone and/or dimethiconol, and at least one aminofunctional silicone. If different silicones are used as a mixture, then the mixing ratio is largely variable. However, preference is given to using all silicones used for the mixture in a ratio of 5:1 to 1:5 in the case of a binary mixture. A ratio of 3:1 to 1:3 is particularly preferred. Very particularly preferred mixtures comprise all silicones present in the mixture as far as possible in a ratio of about 1:1, in each case based on the amounts used in % by weight.

If the silicone mixture is present in the hair treatment compositions and hair aftertreatment compositions according to the invention, then these compositions comprise 0.01 to 10% by weight, preferably 0.1 to 8% by weight, particularly preferably 0.25 to 7.5% by weight and in particular 0.5 to 5% by weight, of silicone mixture, based on the total composition.

Besides ether guanidines according to the invention and the aforementioned optional components, the cosmetic preparations according to the invention for the treatment of the hair after a chemical treatment can also comprise further components which are advantageous and/or customary for the particular intended use.

Thus, shampoos, for example, can comprise 3 to 30% by weight of foaming anionic, zwitterionic, ampholytic and nonionic surfactants. Hair rinses and hair treatments can comprise, for example, 0 to 10% by weight, preferably 0.5 to 5% by weight, of emulsifiers, 0 to 10% by weight, preferably 0.5 to 5% by weight, of consistency regulators and 0 to 20% by weight of cosmetic oils, which may be, for example, of vegetable and/or synthetic origin, emollients, vitamin preparations and/or proteins. Shampoos, hair rinses, hair treatments and reviving compositions can comprise 0 to 8% by weight, preferably 0.1 to 5% by weight, of cationic surfactants and polymers with quaternary ammonium groups for reducing the static chargeability and for improving combability, feel and shine.

Suitable anionic surfactants (E1) in preparations according to the invention are all anionic surface-active substances suitable for use on the human body. These are characterized by a water-solubilizing, anionic group, such as, for example, a carboxylate, sulphate, sulphonate or phosphate group, and a lipophilic alkyl group having about 8 to 30 carbon atoms. Additionally, glycol or polyglycol ether groups, ester, ether and amide groups and also hydroxyl groups may be present in the molecule. Examples of suitable anionic surfactants are, in each case in the form of the sodium, potassium and ammonium salts and also the mono-, di- and trialkanolammonium salts having 2 to 4 carbon atoms in the alkanol group, unbranched and branched fatty acids having 8 to 30 carbon atoms (soaps), ether carboxylic acids of the formula R—O—$(CH_2$—$CH_2O)_x$—$CH_2$—COOH, in which R is an unbranched alkyl group having 8 to 30 carbon atoms and x=0 or 1 to 16, acyl sarcosides having 8 to 24 carbon atoms in the acyl group, acyl taurides having 8 to 24 carbon atoms in the acyl group, acyl isethionates having 8 to 24 carbon atoms in the acyl group, sulphosuccinic acid mono- and dialkyl esters having 8 to 24 carbon atoms in the alkyl group and sulphosuccinic acid monoalkyl polyoxyethyl esters having 8 to 24 carbon atoms in the alkyl group and 1 to 6 oxyethyl groups, unbranched alkanesulphonates having 8 to 24 carbon atoms, unbranched alpha-olefinsulphonates having 8 to 24 carbon atoms, alpha-sulpho-fatty acid methyl esters of fatty acids having 8 to 30 carbon atoms, alkyl sulphates and alkyl polyglycol ether sulphates of the formula R—$O(CH_2$—$CH_2O)X$—$OSO_3H$, in which R is a preferably unbranched alkyl group having 8 to 30 carbon atoms and x=0 or 1 to 12, mixtures of surface-active hydroxysulphonates as in DE-A-37 25 030, sulphated hydroxyalkylpolyethylene and/or hydroxyalkylene propylene glycol ethers as in DE-A-37 23 354, sulphonates of unsaturated fatty acids having 8 to 24 carbon atoms and 1 to 6 double bonds as in DE-A-39 26 344, esters of tartaric acid and citric acid with alcohols, which constitute addition products of about 2-15 molecules of ethylene oxide and/or propylene oxide onto fatty alcohols having 8 to 22 carbon atoms, alkyl and/or alkenyl ether phosphates of the formula (E1-1),

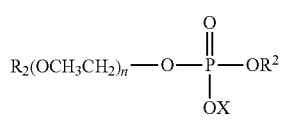
(E1-1)

in which $R^1$ is preferably an aliphatic hydrocarbon radical having 8 to 30 carbon atoms, $R^2$ is hydrogen, a radical $(CH_2CH_2O)_nR^2$ or X, n is numbers from 1 to 10 and X is hydrogen, an alkali metal or alkaline earth metal or $NR^3R^4R^5R^6$, where $R^3$ to $R^6$, independently of one another, are hydrogen or a $C_1$ to $C_4$ hydrocarbon radical, sulphated fatty acid alkylene glycol esters of the formula (E1-2)

$$R^7CO(alkO)_nSO_3M \qquad (E1\text{-}2)$$

in which $R^7CO$— is an unbranched or branched, aliphatic, saturated and/or unsaturated acyl radical having 6 to 22 carbon atoms, alk is $CH_2CH_2$, $CHCH_3CH_2$ and/or $CH_2CHCH_3$, n is numbers from 0.5 to 5 and M is a cation as described in DE-A 197 36 906.5,
monoglyceride sulphates and monoglyceride ether sulphates of the formula (E1-3)

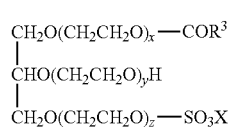
(E1-3)

in which $COR^8$ is an unbranched or branched acyl radical having 6 to 22 carbon atoms, x, y and z are in total 0 or numbers from 1 to 30, preferably 2 to 10, and X is an alkali metal or alkaline earth metal. Typical examples of monoglyceride (ether) sulphates suitable within the context of the invention are the reaction products of lauric acid monoglyceride, coconut fatty acid monoglyceride, palmitic acid monoglyceride, stearic acid monoglyceride, oleic acid monoglyceride and tallow fatty acid monoglyceride, and also ethylene oxide adducts thereof with sulphur trioxide or chlorosulphonic acid in the form of their sodium salts. Preference is given to using monoglyceride sulphates of the formula (E1-3) in which $COR^8$ is an unbranched acyl radical having 8 to 18 carbon atoms, as have been described, for example, in EP-B1 0 561 825, EP-B1 0 561 999, DE-A1 42 04 700 or by A. K. Biswas et al. in J. Am. Oil Chem. Soc. 37, 171 (1960) and F. U. Ahmed in J. Am. Oil Chem. Soc. 67, 8 (1990), amide ether carboxylic acids as described in EP 0 690 044, condensation products of $C_{8-30}$-fatty alcohols with protein hydrolysates and/or amino acids and derivatives thereof, which are known to the person skilled in the art as protein fatty acid condensates, such as, for example, the Lamepon® grades, Gluadin® grades, Hostapon® KCG or the Amisoft® grades.

Preferred anionic surfactants are alkyl sulphates, alkyl polyglycol ether sulphates and ether carboxylic acids having 10 to 18 carbon atoms in the alkyl group and up to 12 glycol ether groups in the molecule, sulphosuccinic acid mono- and dialkyl esters having 8 to 18 carbon atoms in the alkyl group and sulphosuccinic acid monoalkyl polyoxyethyl esters having 8 to 18 carbon atoms in the alkyl group and 1 to 6 oxyethyl groups, monoglyceride sulphates, alkyl and alkenyl ether phosphates, and also protein fatty acid condensates.

Zwitterionic surfactants (E2) is the term used to refer to those surface-active compounds which carry at least one quaternary ammonium group and at least one $COO^{(-)}$ or $—SO_3^{(-)}$ group in the molecule. Particularly suitable zwitterionic surfactants are the so-called betaines, such as the N-alkyl-N,N-dimethylammonium glycinates, for example cocoalkyldimethylammonium glycinate, N-acylamino-propyl-N,N-dimethylammonium glycinates, for example cocoacylaminopropyldimethylammonium glycinate, and 2-alkyl-3-carboxymethyl-3-hydroxyethylimidazolines having in each case 8 to 18 carbon atoms in the alkyl or acyl group, and also cocoacylaminoethyl hydroxyethylcarboxymethyl-glycinate. A preferred zwitterionic surfactant is the fatty acid amide derivative known under the INCI name Cocamidopropyl Betaine.

Ampholytic surfactants (E3) are understood as meaning those surface-active compounds which, apart from a $C_{8-24}$-alkyl or -acyl group in the molecule, contain at least one free amino group and at least one —COOH— or —$SO_3H$ group and are capable of forming internal salts. Examples of suitable ampholytic surfactants are N-alkylglycines, N-alkylaminopropionic acids, N-alkylaminobutyric acids, N-alkyliminodipropionic acids, N-hydroxyethyl-N-alkyl-amidopropylglycines, N-alkyltaurines, N-alkylsarcosines, 2-alkylaminopropionic acids and alkylaminoacetic acids having in each case about 8 to 24 carbon atoms in the alkyl group. Particularly preferred ampholytic surfactants are N-cocoalkylaminopropionate, cocoacyl-aminoethylamino-propionate and $C_{12}$-$C_{18}$-acylsarcosine.

Nonionic surfactants (E4) can contain, as hydrophilic group, e.g. a polyol group, a polyalkylene glycol ether group or a combination of polyol and polyglycol ether group. Such compounds are, for example, addition products of from 2 to 50 mol of ethylene oxide and/or 0 to 5 mol of propylene oxide onto unbranched and branched fatty alcohols having 8 to 30 carbon atoms, onto fatty acids having 8 to 30 carbon atoms and onto alkylphenols having to 15 carbon atoms in the alkyl group, addition products, terminally capped with a methyl or $C_2$-$C_6$-alkyl radical, of from 2 to 50 mol of ethylene oxide and/or 0 to 5 mol of propylene oxide onto unbranched and branched fatty alcohols having 8 to 30 carbon atoms, onto fatty acids having 8 to 30 carbon atoms and onto alkylphenols having 8 to 15 carbon atoms in the alkyl group, such as, for example, the grades available under the trade names Dehydrol® LS, Dehydrol® LT (Cognis), $C_{12}$-$C_{30}$-fatty acid mono- and diesters of addition products of from 1 to 30 mol of ethylene oxide onto glycerol, addition products of from 5 to 60 mol of ethylene oxide onto castor oil and hydrogenated castor oil, polyol fatty acid esters, such as, for example, the commercial product Hydagen® HSP (Cognis) or Sovermol grades (Cognis), alkoxylated triglycerides, alkoxylated fatty acid alkyl esters of the formula (E4-1)

$$R^1CO\text{—}(OCH_2CHR^2)_w OR^3 \quad \text{(E4-1)}$$

in which $R^1CO$ is an unbranched or branched, saturated and/or unsaturated acyl radical having 6 to 22 carbon atoms, $R^2$ is hydrogen or methyl, $R^3$ is unbranched or branched alkyl radicals having 1 to 4 carbon atoms and w is numbers from 1 to 20, amine oxides, hydroxy mixed ethers, as are described, for example, in DE-A 19738866, sorbitan fatty acid esters and addition products of ethylene oxide onto sorbitan fatty acid esters, such as, for example, the polysorbates, sugar fatty acid esters and addition products of ethylene oxide onto sugar fatty acid esters, addition products of ethylene oxide onto fatty acid alkanolamides and fatty amines, sugar surfactants of the alkyl and alkenyl oligoglycoside type according to formula (E4-2), $$R^4O\text{-}[G]_p \quad \text{(E4-2)}$$

in which $R^3$ is an alkyl or alkenyl radical having 4 to 22 carbon atoms, G is a sugar radical having 5 or 6 carbon atoms and p is numbers from 1 to 10. They can be obtained by relevant methods of preparative organic chemistry. By way of representation of the extensive literature, reference may be made here to the overview paper by Biermann et al. in Starch/Stärke 45, 281 (1993), B. Salka in Cosm. Toil. 108, 89 (1993) and J. Kahre et al. in SÖFW-Journal Heft 8, 598 (1995).

The alkyl and alkenyl oligoglycosides can be derived from aldoses or ketoses having 5 or 6 carbon atoms, preferably from glucose. The preferred alkyl and/or alkenyl oligoglycosides are thus alkyl and/or alkenyl oligoglucosides. The index number p in the general formula (E4-II) gives the degree of oligomerization (DP), i.e. the distribution of mono- and oligoglycosides and is a number between 1 and 10. Whereas p in the individual molecule must always be an integer and here can in particular assume the values p=1 to 6, the value p for a specific alkyl oligoglycoside is an analytically determined calculated parameter which in most cases is a fraction. Preference is given to using alkyl and/or alkenyl oligoglycosides with an average degree of oligomerization p of from 1.1 to 3.0. From an applications point of view, preference is given to those alkyl and/or alkenyl oligoglycosides whose degree of oligomerization is less than 1.7 and in particular is between 1.2 and 1.4. The alkyl or alkenyl radical $R^3$ can be derived from primary alcohols having 4 to 11, preferably 8 to 10, carbon atoms. Typical examples are butanol, caproic alcohol, caprylic alcohol, capric alcohol and undecyl alcohol, and also technical-grade mixtures thereof, as are obtained, for example, during the hydrogenation of technical-grade fatty acid methyl esters or in the course of the hydrogenation of aldehydes from the Roelen oxo synthesis. Preference is given to alkyl oligoglucosides of chain length $C_8$-$C_{10}$ (DP=1 to 3) which are produced as forerunning in the distillative separation of technical-grade $C_8$-$C_{18}$-coconut fatty alcohol and may be contaminated with a fraction of less than 6% by weight of $C_{12}$-alcohol, and also alkyl oligoglucosides based on technical-grade $C_{9/11}$-oxo alcohols (DP=1 to 3). Furthermore, the alkyl or alkenyl radical $R^3$ can also be derived from primary alcohols having 12 to 22, preferably 12 to 14, carbon atoms. Typical examples are lauryl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol, and technical-grade mixtures thereof which can obtained as described above. Preference is given alkyl oligoglucosides based on hydrogenated $C_{12/14}$-coconut alcohol with a DP of from 1 to 3.

Sugar surfactants of the type of fatty acid N-alkylpolyhydroxyalkylamides, a nonionic surfactant of the formula (E4-3), $$R^5CO\text{—}NR^6\text{—}[Z] \quad \text{(E4-3)}$$

in which $R^5CO$ is an aliphatic acyl radical having 6 to 22 carbon atoms, $R^6$ is hydrogen, an alkyl or hydroxyalkyl radical having 1 to 4 carbon atoms and [Z] is an unbranched or branched polyhydroxyalkyl radical having 3 to 12 carbon atoms and 3 to 10 hydroxyl groups are also suitable non-ionic surfactants. The fatty acid N-alkylpolyhydroxyalkylamides are known substances which can usually be obtained by reductive amination of a reducing sugar with ammonia, an alkylamine or an alkanolamine and subsequent acylation with a fatty acid, a fatty acid alkyl ester or a fatty acid chloride. With regard to the processes for their preparation, reference may be made to the U.S. Pat. No. 1,985,424, U.S. Pat. No. 2,016,962 and U.S. Pat. No. 2,703,798, and also the international Patent Application WO 92/06984. An overview of this topic by H. Kelkenberg can be found in Tens. Surf. Det. 25, 8 (1988). Preferably, the fatty acid N-alkylpolyhydroxy-alkylamides are derived from reducing sugars having 5 or 6 carbon atoms, in particular from glucose. The preferred fatty acid N-alkylpolyhydroxyalkylamides are therefore fatty acid N-alkylglucamides, as given by the formula (E4-4):

$$R^7CO\text{—}NR^8\text{—}CH_2\text{—}(CHOH)_4\text{—}CH_2OH \quad \text{(E4-4)}$$

As fatty acid N-alkylpolyhydroxyalkylamides, preference is given to using glucamides of the formula (E4-4) in which $R^8$ is hydrogen or an alkyl group and $R^7CO$ is the acyl radical of caproic acid, caprylic acid, capric acid, lauric acid, myristic acid, palmitic acid, palmoleic acid, stearic acid, isostearic acid, oleic acid, elaidic acid, petroselic acid, linoleic acid, linolenic acid, arachic acid, gadoleic acid, behenic acid or erucic acid or technical-grade mixtures thereof. Particular preference is given to fatty acid N-alkylglucamides of the formula (E4-4) which are obtained by reductive amination of glucose with methylamine and subsequent acylation with lauric acid or $C_{12/14}$-coconut fatty acid or a corresponding derivative. Furthermore, the polyhydroxy-alkylamides can also be derived from maltose and palatinose.

The cationic surfactants may be, for example,
  quaternary ammonium compounds, such as, for example, alkyltrimethylammonium salts, dialkyldimethylammonium salts, trialkylmethylammonium salts and imidazolinium compounds. The long alkyl chains consist of a carbon chain having 10 to 22 carbon atoms, the counterions to the quaternary nitrogen are e.g. halides, sulphate, methosulphate, acetate, lactate, glycolate, nitrate or phosphate. Products are available commercially under the name Varisoft 300, 432 CG, 442-100 P, BT 85 from Evonik Goldschmidt, Dehyquart® A from Cognis or Arquad® 16-50, 2HT-75 from Akzo Nobel;

ester quats, i.e. compounds which contain both at least one ester function and also at least one quaternary ammonium group as structural element. Preferred ester quats are quaternized ester salts of fatty acids with triethanolamine, quaternized ester salts of fatty acids with diethanolalkylamines and quaternized ester salts of fatty acids having 1,2-dihydroxypropyldialkylamines. Such products are sold, for example, under the trade names Stepantex®, Dehyquart® (Cognis) and Armocare® (Akzo Nobel). The products Armocare® VGH-70, an N,N-bis(2-palmitoyl-oxyethyl)dimethylammonium chloride, and also Dehyquart® F-75, Dehyquart® C-4046, Dehyquart® L80 and Dehyquart® AU-35 (Cognis) are examples of such ester quats;

alkylamido quats, as are commercially, available, under the name Varisoft® PATC and RTM 50 from Evonik Goldschmidt;

alkylamidoamines, which are usually prepared by amidation of natural or synthetic fatty acids and fatty acid cuts with dialkylaminoamines and are available, for example, under the name Tegoamid® S 18 from Evonik Goldschmidt.

The polymers with quaternary ammonium groups may be, for example, cationic cellulose derivatives, as are commercially available under the name Celquat® H 100 and L 200 from National Starch or Polymer JR® 400 from Amerchol, polymeric dimethyldiallylammonium salts and copolymers thereof with esters and amides of acrylic acid and methacrylic acid. The products commercially available under the name Merquat® 100 or Merquat® 550 from Calgon are examples of such cationic polymers, copolymers of vinylpyrrolidone with quaternized derivatives of dialkylaminoacrylate and -methacrylate. Such compounds are commercially available under the name Gafquat® 735 and Gafquat® 744 from ISP, vinylpyrrolidone-vinylimidazolium methochloride copolymers, as are supplied under the name Luviquat® FC 370, FC 550, FC 905 and HM-552 from BASF, quaternized polyvinyl alcohol, quaternized protein hydrolysates of animal or vegetable origin based on keratin, collagen, elastin, wheat, rice, soya, milk, silk, corn. Such products are sold under the name Croquat® Wheat and Silk by Croda, Promois® W-32CAQ, Silk CAQ, WG CAQ by Seiwa Kasei or Quat-Coll® CDMA by Brooks, guar hydroxypropyltrimethylammonium chloride, aminofunctional polydimethylsiloxanes or hydroxylamino-modified silicones, such as the commercial products ABIL® Quat 3272 and ABIL® Quat 3474 from Evonik Goldschmidt, Dow Corning® 929 Emulsion, Dow Corning® 939 from Dow Corning.

If the hair treatment compositions and hair aftertreatment compositions according to the invention are, for example, setting formulations or other hairstyling preparations, these can comprise, for example, 0.1 to 5% by weight of film-forming polymers that are soluble in aqueous or aqueous-alcoholic media, optionally together with cationic surfactants or cationic polymers. Examples of film formers are, for example, homopolymers of vinylpyrrolidone, homopolymers of N-vinylformamide, copolymers of vinylpyrrolidone and vinyl acetate, terpolymers of vinylpyrrolidone, vinyl acetate and vinyl propionate, polyacrylamides, polyvinyl alcohols, high molecular weight polyethylene glycol or high molecular weight copolymers of ethylene glycol with propylene glycol, chitosan. These products are commercially available under the name Luviskol® K30, K60, K80, VA37E from BASF oer PVP/VA E335 and PVP K30 from ISP.

Typical guide formulations for the respective applications belong to the known prior art and are contained, for example, in the brochures of the manufacturers of the respective base materials and active ingredients. These existing formulations can generally be adopted unchanged. If necessary, however, the desired modifications for adaptation and/or optimization can be undertaken without complications through simple experiments.

In a preferred embodiment of the invention, the hair treatment compositions and hair aftertreatment compositions according to the invention which have the ether guanidines according to the invention also comprise, besides the ether guanidines, from 0 to 10% by weight, preferably from 0.1 to 7.5% by weight, of one or more emulsifiers, from 0 to 10% by weight, preferably from 0.1 to 7.5% by weight, of one or more consistency regulators, from 0.1 to 7.5% by weight, preferably 0.1 to 5% by weight, of one or more of the aforementioned cationic surfactants and/or polymers with one or more quaternary ammonium groups and/or from 0 to 20% by weight, preferably from 0.1 to 17.5% by weight of one or more cosmetic oils or emollients, and optionally customary auxiliaries and additives in customary concentrations. The remainder can be, for example, water (ad 100% by weight water). In a particularly preferred embodiment of the invention, the hair treatment compositions and hair aftertreatment compositions according to the invention comprise, as cationic surfactants and/or polymers with one or more quaternary ammonium groups, one or more compounds selected from the group comprising cetrimonium chloride, dicetyldimonium chloride, behentrimonium chloride, distearyldimonium chloride, behentrimonium methosulphate, distearoylethyldimonium chloride, palmitamido-propyltrimonium chloride, guar hydroxypropyltrimonium chloride, hydroxypropylguar hydroxypropyltrimonium chloride, or quaternium-80 or else amine derivatives, such as, for example, aminopropyldimethicones or stearamidopropyldimethylamines.

Such preferred compositions are in particular suitable to be used as hair rinse, intensive treatment, leave-in hair rinse or shampoo.

A typical formulation of a hair rinse/hair treatment comprises, for example:
a) 0.1 to 2.5% by weight of at least one of the compounds of the general formula (I),
b) 0.1 to 5% by weight of emulsifier,
c) 0.1 to 5% by weight of consistency regulator,
d) 0.1 to 5% by weight of cationic surfactants and/or polymers with quaternary ammonium groups,
e) 0 to 10% by weight of other cosmetic active ingredients, preservatives, and customary additives and auxiliaries,
f) ad 100% by weight water.

A typical formulation of a hair shampoo comprises, for example:
a) 0.1 to 2.5% by weight of at least one of the compounds of the general formula (I),
b) 3 to 30% by weight of foaming anionic, amphoteric, ampholytic and/or nonionic surfactants,
c) 0.1 to 5.0% by weight of cationic surfactants and/or polymers with quaternary ammonium groups,
d) 0.1 to 6.0% by weight of thickeners,
e) 0 to 10% by weight of other cosmetic active ingredients, opacifiers, solvents and customary additives and auxiliaries,
f) ad 100% by weight water.

The hair treatment compositions and hair aftertreatment compositions according to the invention for the chemical treatment of hair may be, for example, compositions for the permanent shaping of the hair, such as permanent waving compositions and neutralizing compositions or hair smoothing compositions, colour-changing compositions, such as blonding compositions, oxidation colorants and tinting compositions and shampoos based on direct dyes.

Besides the ether guanidines according to the invention and salts thereof, the preparations according to the invention for the chemical treatment of the hair can also comprise further components which are customarily used for the particular application.

For a permanent wave solution these may be, for example, 1 to 10% by weight of thioglycolic acid, thioglycolic acid salts or esters. Permanent wave neutralizers or blonding compositions comprise preferably 2 to 10% by weight of oxidizing agent, such as, for example, potassium bromate, sodium bromate or hydrogen peroxide. Hair smoothing compositions are preferably based on the use of strong bases or on reducing agents such as, for example, thioglycolic acid salts or guanidinium carbonate. Hair colorants preferably comprise direct hair colorants or oxidation dye precursors.

The direct dyes are preferably selected from the nitrophenylenediamines, the nitroaminophenols, the azo dyes, the anthraquinones or the indophenols. Particularly preferred direct dyes are the compounds known under the international names or trade names HC Yellow 2, HC Yellow 4, HC Yellow 5, HC Yellow 6, HC Yellow 12, Acid Yellow 1, Acid Yellow 10, Acid Yellow 23, Acid Yellow 36, HC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red 57:1, HC Blue 2, HC Blue 12, Disperse Blue 3, Acid Blue 7, Acid Green 50, HC Violet 1, Disperse Violet 1, Disperse Violet 4, Acid Violet 43, Disperse Black 9, Acid Black 1 and Acid Black 52, and also 1,4-diamino-2-nitrobenzene, 2-amino-4-nitrophenol, 1,4-bis(β-hydroxyethyl)amino-2-nitrobenzene, 3-nitro-4-(β-hydroxyethyl)aminophenol, 2-(2'-hydroxyethyl)amino-4,6-dinitrophenol, 1-(2'-hydroxyethyl)amino-4-methyl-2-nitrobenzene, 1-amino-4-(2'-hydroxyethyl)amino-5-chloro-2-nitrobenzene, 4-amino-3-nitrophenol, 1-(2'-ureidoethyl)amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid and 2-chloro-6-ethylamino-1-hydroxy-4-nitrobenzene.

The hair treatment compositions and hair aftertreatment compositions according to the invention can comprise further cosmetic auxiliaries and additives which are customary in such preparations. Such auxiliaries are, for example, solubility promoters such as ethanol, isopropanol, ethylene glycol, propylene glycol, glycerol and diethylene glycol, complexing agents such as EDTA, NTA, β-alaninediacetic acid and phosphonic acid, preservatives, antioxidants, fragrances, dyes for colouring the cosmetic preparation, opacifiers such as latex, styrene/PVP and styrene-acrylamide copolymers, pearlizing agents such as ethylene glycol mono- and distearate and PEG-3 distearate, pigments, photo-protective agents, thickeners and/or propellants.

The preparation of the hair treatment compositions and hair aftertreatment compositions according to the invention can take place in the usual manner, where the ether guanidines may be dissolved either in the aqueous phase or else in the oil phase. The pH can preferably be adjusted last by adding the acid and/or buffer mixture envisaged for this purpose.

The ether guanidines according to the invention and/or the hair treatment compositions and hair aftertreatment compositions according to the invention can be used, for example, for producing hair shampoo, leave-in formulations or as active component in cosmetic formulations with antidandruff effect. On account of their mild microbiocidal effect, the ether guanidines of the general formula (I) can be used or co-used in particular as active ingredients in mild antidandruff formulations.

Some preparation examples and formulations are listed below. These illustrate the subject matter of the invention and do not limit it.

EXAMPLES

Unless noted otherwise, all of the quantitative data in % are parts by weight.

Example 1

Synthesis of $C_{12-15}$-oxypropylguanidinium chloride 271 g of Tomamine® PA-19 were dissolved with stirring in 100 ml of n-butanol. Then, 86.4 g of hydrochloric acid (38% strength) were added and the mixture was slowly heated. After reaching the reaction temperature of 95° C., a solution of 42 g of cyanamide in 240 ml of n-butanol was added dropwise over a period of 1 h and the mixture was further stirred for 2 h at 95° C. The solvent was then stripped off under reduced pressure (ca. 1-2 mbar). The crude product was recrystallized from 325 ml of ethyl acetate and crystallized at 10° C. The end product was in the form of a crystalline colourless powder.

$C_{12-15}$-Oxypropylguanidinium chloride: $^{13}$C-NMR, 100 MHz, $CD_3OD$, 25° C.: δ=158.6 (1C, $C_{guanidinium\ gr.}$), 72.0 (1C, $OCH_2$), 68.4 (1C, $OCH_2$), 39.7 (1C, $NHCH_2$), 33.0 (1C, $CH_2$), 30.8 (5-8C, $CH_2$), 30.6 (1C, $CH_2$), 30.4 (1C, $CH_2$), 30.1 (1C, $CH_2$), 27.2 (1C, $CH_2$), 23.7 (1C, $CH_2$), 14.7 (1C, $CH_3$)

The other ether guanidines were prepared analogously on the basis of the Tomamines® PA14, PA1618 and PA17.

Example 2

Application-Related Testing

Hair Used:
Euro-hair (hair from Europeans), left natural.
Predamage of the Hair:
In each case 1× permanent wave and bleaching using standard commercial products.
Treatment of the Damaged Hair:
The damaged hair was treated with the example formulations. To prepare the formulations, customary formulation processes known to the person skilled in the art were used. The compositions of the formulations are given in Tables 1 and 2.

TABLE 1

Formulations of hair rinses (data in % by weight)

|  | Hair rinse A | Hair rinse B (not according to the invention) |
|---|---|---|
| Ether guanidine (according to formula I) | 2.0 | — |
| TEGINACID ® C, Evonik Goldschmidt GmbH (INCI: Ceteareth-25) | 0.5 | 0.5 |

TABLE 1-continued

Formulations of hair rinses (data in % by weight)

|  | Hair rinse A | Hair rinse B (not according to the invention) |
|---|---|---|
| TEGO ® alkanol 1618, Evonik Goldschmidt GmbH (INCI: Cetearyl Alcohol) | 2.0 | 2.0 |
| HCl | ad pH = 5.5 | ad pH = 5.5 |
| Water | ad 100 | ad 100 |

TABLE 2

Formulations of hair shampoos (data in % by weight)

|  | Hair shampoo C | Hair shampoo D (not according to the invention) |
|---|---|---|
| Ether guanidine (according to formula I) | 0.5 | — |
| Texapon ® NSO, 28% strength, Cognis (INCI: Sodium Laureth Sulfate) | 27 | 27 |
| TEGO ® Betain F50, 37.5% strength, Evonik Goldschmidt GmbH (INCI: Cocamidopropyl Betaine) | 8 | 8 |
| Jaguar ® Excel, Rhodia (INCI: Guarhydroxypropyl Trimonium Chloride) | 0.1 | 0.1 |
| Ucare ® Polymer JR400, Dow Amerchol (INCI: Polyquaternium-10) | 0.3 | 0.3 |
| Sodium chloride | 1.2 | 1.2 |
| Water | ad 100 | ad 100 |

The improvement in the mechanical resistance of damaged hair through alkyl guanidinium compounds was ascertained by a pairwise comparison of individual hairs before and after treatment with the test formulation.

For each test formulation, 30 wet individual hairs were measured. The experimental procedure was as follows:
1. The predamaged hairs were wetted with water and, using the fully automated device Mtt670 from DiaStron, the force was measured which is required for 15% elongation.
2. The hairs were immersed for recovery in a waterbath for at least 30 min.
3. Then, the hairs were immersed for 30 min in the test formulation and then each hair was rinsed for ca. 7 s under running water.
4. The hairs were left overnight (=12 h) to dry in the air.
5. The force which was required in order to elongate the treated hairs by 15% was again measured as described above, after wetting with water.
6. The difference in the 15% elongation forces ($\Delta E$ 15%) before and after treatment with the test formulation was calculated and used as a measure of the improvement in the mechanical resistance of the damaged hairs through the alkylguanidine compounds.

For the statistical assessment of the measurement values, the t-test for the pairwise comparison both of the measurement values before and after the treatment and also of the measurement values of the treated hair with the result of the placebo result were used. This enables a statement to be made about the statistical certainty of the measurement values (in this respect see also: R. E. Kaiser, J. A. Mühlbauer, "Elementare Tests zur Beurteilung von Meβdaten" [Elemental tests for assessing measurement data], B. I. Wissenschaftsverlag, Mannheim 1983). For a statistical certainty of >95%, it is assumed that there is a significant difference, >99% means that the measurement values differ with high significance, >99.9 that they differ with the highest significance.

The values which were obtained when determining the force for elongation of individual hairs by 15% before and after their treatment (at least 30 independent measurements) are given in Tables 3 and 4.

TABLE 3

| Formulation as in Table 1 | $\Delta E$ 15% [mN] |
|---|---|
| A ($R^3$ = C12-15, 20% branched C chain) | 6.4 |
| A ($R^3$ = iso-C13, 100% branched C chain) | 2.5 |
| A ($R^3$ = C12/14, 100% unbranched C chain) | 5.3 |
| B (placebo) | 3.7 |

TABLE 4

| Formulation as in Table 2 | $\Delta E$ 15% [mN] |
|---|---|
| C ($R^3$ = C12-15, 20% branched C chain) | 2.9 |
| C ($R^3$ = iso-C10, 100% branched C chain) | 1.0 |
| C ($R^3$ = C12/14, 100% unbranched C-chain) | 2.4 |
| D (placebo) | 2.3 |

A random sampling-type testing of the significance of the values revealed that a statistically significant difference of >95% is present.

Example 3

Testing the Hair Sensorics

Hair rinses with and without ether guanidines were compared, and sensorily evaluated with regard to the properties
detangleability, wet
feel, wet
combability, wet
feel, dry
combability, dry and
volume
on undamaged hair. The formulations are given in Table 5:

TABLE 5

Formulations for testing the hair sensorics (data in % by weight)

| Formulation examples | 3-1 | 3-2 | 3-3 (control) |
|---|---|---|---|
| Ether guanidine (as in formula I), ($R^3$ = C12-15) | 1.0 | 0.5 | — |
| Varisoft ® 300, 30% strength, Evonik Goldschmidt GmbH (INCI: Cetrimonium Chloride) | — | 1.6 | — |
| TEGO ® alkanol 16, Evonik Goldschmidt GmbH (INCI: Cetyl Alcohol) | 5 | 5 | 5 |
| TEGINACID ® C, Evonik Goldschmidt GmbH (INCI: Ceteareth-25) | 0.5 | 0.5 | 0.5 |
| Preservative | 0.45 | 0.45 | 0.45 |
| Water | ad 100 | ad 100 | ad 100 |

The assessment was made by 4 trained test persons on a scale from 1 to 5 (1=very poor, 2=poor, 3=average, 4=good, 5=very good). The average values were formed from the individual assessments. The results are given in Table 6.

TABLE 6

Results of the sensorics test

|  | Formulation 3-1 | Formulation 3-2 | Formulation 3-3 |
|---|---|---|---|
| Detangleability, wet | 4.7 | 4.4 | 1.8 |
| Feel, wet | 3.8 | 4.5 | 1.3 |
| Combability, wet | 4.7 | 4.6 | 1.8 |
| Feel, dry | 4.7 | 5.0 | 4.0 |
| Combability, dry | 4.8 | 5.0 | 3.8 |
| Volume | 1.8 | 1.8 | 4.0 |

Example 4

Further Formulation Examples

The examples below are intended to show that the ether guanidines according to the invention can be used in a multitude of different cosmetic formulations.

TABLE EXAMPLE 4.1

Shampoo for damaged hair

| Formulation constituents | % by wt. |
|---|---|
| Texapon ® NSO IS T, ca. 27% strength, Cognis (INCI: Sodium Laureth Sulfate) | 32.0 |
| TEGO ® Betain F 50, 37.5% strength, Evonik Goldschmidt GmbH (INCI: Cocamidopropyl Betaine) | 8.0 |
| VARISOFT ® PATC, ca. 60% strength, Evonik Goldschmidt GmbH (INCI: Palmitamidopropyltrimonium Chloride | 1.5 |
| Ether guanidine (as in formula I), ($R^3$ = C12-15), 20% branched C chain | 1.0 |
| Preservative | 0.6 |
| Perfume | 0.3 |
| Demin. water | ad 100 |

TABLE EXAMPLE 4.2

Leave-in hair rinse

| Formulation constituents | % by wt. |
|---|---|
| TAGAT ® CH 40, Evonik Goldschmidt GmbH (INCI: PEG-40 Hydrogenated Castor Oil) | 0.5 |
| TEGO ® Betain F 50, 37.5% strength, Evonik Goldschmidt GmbH (INCI: Cocamidopropyl Betaine) | 2.0 |
| VARISOFT ® 300, 30% strength, Evonik Goldschmidt GmbH (INCI: Cetrimonium Chloride) | 1.3 |
| Ether guanidine (as in formula I), ($R^3$ = C12-15), 20% branched C chain | 1.0 |
| ABIL ® Quat 3272, ca. 50% strength, Evonik Goldschmidt GmbH (INCI: Quaternium-80) | 0.6 |
| TEGOCEL ® HPM 50, Evonik Goldschmidt GmbH (INCI: Hydroxypropyl Methylcellulose) | 0.3 |
| Citric acid, 30% strength | 0.1 |
| Perfume | 0.3 |
| Preservative | 0.6 |
| Demin. water | 93.3 |

TABLE EXAMPLE 4.3

Shampoo, PEG & sulphate free

| Formulation constituents | % by wt. |
|---|---|
| REWOTERIC ® AM C, Evonik Goldschmidt GmbH (INCI: Sodium Cocoamphoacetate) | 15.0 |
| TEGO ® Betain F 50, 37.5% strength, Evonik Goldschmidt GmbH (INCI: Cocamidopropyl Betaine) | 7.0 |
| REWOPOL ® SB F 12 P, Evonik Goldschmidt GmbH (INCI: Disodium Lauryl Sulfosuccinate) | 3.2 |
| ANTIL ® HS 60, Evonik Goldschmidt GmbH (INCI: Cocamidopropyl Betaine, Glyceryl Laurate) | 3.0 |
| TEGOSOFT ® LSE 65 K soft, Evonik Goldschmidt GmbH (INCI: Sucrose Cocoate) | 2.5 |
| Citric acid, 30% strength | 2.0 |
| Ether guanidine (as in formula I), ($R^3$ = C12-15), 20% branched C chain | 0.5 |
| Perfume | 0.3 |
| Preservative | 0.6 |
| Demin. water | ad 100 |

TABLE EXAMPLE 4.4

Intensive treatment

| Formulation constituents | % by wt. |
|---|---|
| TEGO ® alkanol 1618, Evonik Goldschmidt GmbH (INCI: Cetearyl Alcohol) | 4.4 |
| VARISOFT ® EQ 65, Evonik Goldschmidt GmbH (INCI: Distearoyl Dimonium Chloride, Cetearyl Alcohol) | 3.2 |
| Glycerol | 2.0 |
| TEGINACID ® C, Evonik Goldschmidt GmbH (INCI: Ceteareth-25) | 0.5 |
| Ether guanidine (as in formula I), ($R^3$ = C12-15), 20% branched C chain | 0.5 |
| Perfume | 0.3 |
| Preservative | 0.5 |
| Demin. water | ad 100 |

TABLE EXAMPLE 4.5

Hair rinse for damaged hair

| Formulation constituents | % by wt. |
|---|---|
| ABIL ® Soft AF 100, Evonik Goldschmidt GmbH (INCI: Methoxy PEG/PPG-7/3 Aminopropyl Dimethicone | 3.2 |
| TEGO ® alkanol 16, Evonik Goldschmidt GmbH (INCI: Cetyl Alcohol) | 4.0 |
| Glycerol | 2.0 |
| VARISOFT ® BT 85, Evonik Goldschmidt GmbH (INCI: Behentrimonium Chloride) | 1.0 |
| Ether guanidine (as in formula I), ($R^3$ = C12-15), 20% branched C chain | 0.5 |
| Perfume | 0.3 |
| Preservative | 0.6 |
| Demin. water | ad 100 |

All of the formulations of Examples 4.1 to 4.5 exhibited the stabilities customary for the respective applications.

The invention claimed is:

1. A mixture of ether guanidine compounds having the following formula:

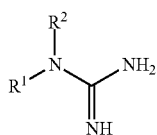

and/or salts or hydrates thereof, wherein:
$R^1$ is —$CH_2$—$CH_2$—$CH_2$—O—$R^3$ wherein $R^3$ is selected from hydrocarbon groups having 12 to 15 carbon atoms, wherein 15-25% by weight of the mixture of the ether guanidine compounds has groups $R^3$ that are branched and
$R^2$ is a hydrogen atom.

2. The mixture of ether guanidine compounds according to claim 1, wherein said ether guanidines are in salt form and the salt is at least one of an organic or inorganic acid selected from the group consisting of formic acid, acetic acid, propionic acid, butanoic acid, isobutanoic acid, hexanoic acid, heptanoic acid, octanoic acid, caprylic acid, nonanoic acid, capric acid, undecanoic acid, lauric acid, myristic acid, palmitic acid, stearic acid, arachic acid, behenic acid, cyclopentanecarboxylic acid, cyclohexanecarboxylic acid, acrylic acid, methacrylic acid, vinylacetic acid, isocrotonic acid, crotonic acid, 2-/3-/4-pentenoic acid, 2-/3-/4-/5-hexenoic acid, lauroleic acid, myristoleic acid, palmitoleic acid, oleic acid, gadoleic acid, sorbic acid, linoleic acid, linolenic acid, pivalic acid, ethoxyacetic acid, phenylacetic acid, glycolic acid, lactic acid, cinnamic acid, sorbic acid, nicotinic acid, urocanic acid, pyrrolidonecarboxylic acid, 2-ethylhexanoic acid, oxalic acid, malic acid, malonic acid, succinic acid, tartaric acid, glutaric acid, citric acid, adipic acid, pimelic acid, suberic acid, azelaic acid, sebacic acid, maleic acid, fumaric acid, benzoic acid, o-/m-/p-toluic acid, o-/m-/p-hydroxybenzoic acid, salicylic acid, 3-/4-hydroxybenzoic acid, phthalic acid, terephthalic acid, hexahydro- or tetrahydrophthalic acid, glycine, alanine, beta-alanine, valine, leucine, phenylalanine, tyrosine, serine, threonine, methionine, cysteine, cystine, proline, hydroxyproline, pipecolic acid, tryptophan, aspartic acid, asparagine, glutamic acid, glutamine, lysine, histidine, ornithine, arginine, aminobenzoic acid, methanesulphonic acid, trifluoromethanesulphonic acid, benzenesulphonic acid, p-toluenesulphonic acid, carbonic acid, phosphoric acid, hydrochloric acid, hydrobromic acid, hydroiodic acid, hydrofluoric acid, perchloric acid, nitric acid, and sulphuric acid, and mixtures thereof.

3. A hair treatment and aftertreatment composition, wherein said composition has, as an active substance, the mixture of ether guanidine compounds according to claim 1.

4. The composition according to claim 3, wherein said composition comprises 0.01 to 10.0% by weight of the mixture of ether guanidine compounds.

5. The composition according to claim 3, further comprising 0 to 10% by weight of one or more emulsifiers, 0 to 10% by weight of one or more consistency regulators, 0 to 10% by weight of one or more surfactants and/or 0 to 20% by weight of one or more cosmetic oils or emollients.

6. The composition according to claim 3, further comprising one or more hair cosmetic active ingredients, antidandruff active ingredients, vitamins, panthenol, pyrrolidonecarboxylic acid, bisabolol, plant extracts, creatine and/or ceramides.

7. A hair care product comprising a mixture of ether guanidine compounds having the following formula:

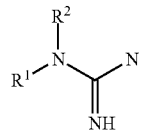

and/or salts or hydrates thereof, wherein:
$R^1$ is —$CH_2$—$CH_2$—$CH_2$—O—$R^3$ wherein $R^3$ is selected from hydrocarbon groups having 12 to 15 carbon atoms, wherein 15-25% by weight of the mixture of the ether guanidine compounds has radicals $R^3$ that are branched, and
$R^2$ is a hydrogen atom.

8. A method of treating hair containing dandruff, said method comprising applying a hair care product according to claim 7 to said hair, wherein said hair care product has an antidandruff effect.

* * * * *